US010213412B2

(12) United States Patent
Greenberg et al.

(10) Patent No.: US 10,213,412 B2
(45) Date of Patent: Feb. 26, 2019

(54) MODULATORS OF $CA^{2+}$ RELEASE-ACTIVATED $CA^{2+}$ (CRAC) CHANNELS AND PHARMACEUTICAL USES THEREOF

(71) Applicant: Vivreon Biosciences, LLC, San Diego, CA (US)

(72) Inventors: Milton L. Greenberg, Costa Mesa, CA (US); John T. Ransom, Encinitas, CA (US); Clayton A. White, Costa Mesa, CA (US); Omed S. Muzaffery, Irvine, CA (US); Andrew C. Newman, San Diego, CA (US)

(73) Assignee: VIVREON BIOSCIENCES, LLC, San Diego, CA (US)

( * ) Notice: Subject to any disclaimer, the term of this patent is extended or adjusted under 35 U.S.C. 154(b) by 21 days.

(21) Appl. No.: 15/539,088

(22) PCT Filed: Jan. 11, 2016

(86) PCT No.: PCT/US2016/012909
§ 371 (c)(1),
(2) Date: Jun. 22, 2017

(87) PCT Pub. No.: WO2016/115054
PCT Pub. Date: Jul. 21, 2016

(65) Prior Publication Data

US 2018/0263960 A1 Sep. 20, 2018

Related U.S. Application Data

(60) Provisional application No. 62/103,033, filed on Jan. 13, 2015.

(51) Int. Cl.

| | |
|---|---|
| ***C07D 207/33*** | (2006.01) |
| ***C07D 207/333*** | (2006.01) |
| ***A61K 31/4025*** | (2006.01) |
| ***A61K 45/06*** | (2006.01) |
| ***A61P 1/16*** | (2006.01) |
| ***A61P 13/12*** | (2006.01) |
| ***A61P 29/00*** | (2006.01) |
| ***A61P 35/02*** | (2006.01) |

(52) U.S. Cl.
CPC .......... *A61K 31/4025* (2013.01); *A61K 45/06* (2013.01); *A61P 1/16* (2018.01); *A61P 13/12* (2018.01); *A61P 29/00* (2018.01); *A61P 35/02* (2018.01); *C07D 207/33* (2013.01); *C07D 207/333* (2013.01)

(58) Field of Classification Search
None
See application file for complete search history.

(56) References Cited

U.S. PATENT DOCUMENTS

| | | | |
|---|---|---|---|
| 4,644,009 | A | 2/1987 | Huang et al. |
| 5,041,442 | A | 8/1991 | Romero et al. |
| 6,063,782 | A | 5/2000 | Kimura et al. |

FOREIGN PATENT DOCUMENTS

| | | | |
|---|---|---|---|
| WO | WO-9317671 | A1 | 9/1993 |
| WO | WO-2016115054 | A2 | 7/2016 |

OTHER PUBLICATIONS

Berge et al. Pharmaceutical Salts. Journal of Pharmaceutical Sciences 66(1):1-19 (Jan. 1977).
Bundgaard. Advanced Drug Delivery Review 8:1-38 (1992).
Bundgaard. Design and Application of Prodrugs. Textbook of Drug Design and Development. Krosgaard-Larsen and Bundgaard. Chapter 5. pp. 113-191 (1991).
PCT/US2016/012909 International Search Report and Written Opinion dated Jul. 14, 2016.
Perez et al. Highly potent, chemically stable quorum sensing agonist s for Vibrio cholerae. Chem Sci 5(1):151-155 (2014).
Widder et al. Section III: Prodrugs Kinetics. Method in Enzymology. 112:309-396 (1985).

*Primary Examiner* — Alicia L Otton
(74) *Attorney, Agent, or Firm* — Wilson Sonsini Goodrich & Rosati

(57) ABSTRACT

Described herein are compounds that modulate the activity of CRAC channels, methods of making such compounds, pharmaceutical compositions, and medicaments containing such compounds, and methods of using such compounds in the treatment of conditions, diseases, or disorders associated with CRAC channel activity.

20 Claims, 10 Drawing Sheets

MODULATORS OF CA$^{2+}$ RELEASE-ACTIVATED CA$^{2+}$ (CRAC) CHANNELS AND PHARMACEUTICAL USES THEREOF

CROSS-REFERENCE TO RELATED APPLICATIONS

This application is the U.S. National Phase application of International Application No. PCT/US2016/012909, filed Jan. 11, 2016, and claims the benefit of U.S. Provisional Application No. 62/103,033, filed Jan. 13, 2015, all of which are hereby incorporated by reference in their entirety.

FIELD OF THE INVENTION

Described herein are compounds that are modulators of Ca$^{2+}$ release-activated Ca$^{2+}$ (CRAC) channel activity, methods of making such compounds, pharmaceutical compositions and medicaments comprising such compounds, and methods of using such compounds in the treatment of conditions, diseases, or disorders associated with Ca$^{2+}$ release-activated Ca$^{2+}$ (CRAC) channel activity.

BACKGROUND OF THE INVENTION

The Ca$^{2+}$ release-activated Ca$^{2+}$ (CRAC) channel is an essential ion channel in the store operated Ca$^{2+}$ (SOC) channel family. The CRAC channel is comprised of a complex of plasma membrane-resident Orai and endoplasmic reticulum-resident stromal interaction molecule (STIM) proteins. Orai1, Orai2, and Orai3 are members of the Orai family of proteins. Orai1 is expressed on the plasma membrane and is the principle Ca$^{2+}$-selective pore-forming channel subunit in human leukocytes. Orai signaling is implicated in, for example, cancer, immunological diseases, and neurological diseases.

SUMMARY OF THE INVENTION

Compounds described herein are inhibitors of CRAC channel activity. In some embodiments, the compounds described herein are inhibitors of Orai Ca$^{2+}$ channel activity. In some embodiments, the inhibitors described herein are useful as agents for the treatment or prevention of diseases or conditions in which CRAC and/or Orai channels participates, is involved in the etiology or pathology of the disease, or is otherwise associated with at least one symptom of the disease. Inhibition of the physiological activity of CRAC and/or Orai Ca$^{2+}$ channels is useful in a variety of diseases or conditions. CRAC channel and Orai Ca$^{2+}$ channel signaling has been implicated in cancer, immunological diseases, and neurological diseases.

Compounds described herein are used in the treatment of diseases or conditions in which CRAC channel activity contributes to the symptomology or progression of the disease, disorder or condition. In one aspect, the methods, compounds, pharmaceutical compositions, and medicaments described herein comprise CRAC channel inhibitors. Also, compounds described herein are used in the treatment of diseases or conditions in which Orai Ca$^{2+}$ channel activity contributes to the symptomology or progression of the disease, disorder or condition. In one aspect, the methods, compounds, pharmaceutical compositions, and medicaments described herein comprise Orai Ca$^{2+}$ channel inhibitors.

In one aspect, described herein is a compound of Formula (I), or a pharmaceutically acceptable salt, or solvate thereof:

Formula (I)

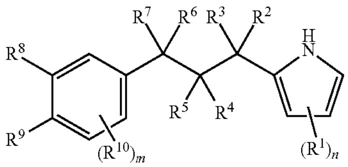

wherein, each $R^1$ is independently H, halogen, $C_1$-$C_6$alkyl, $C_1$-$C_6$fluoroalkyl, $C_1$-$C_6$deuteroalkyl, $C_3$-$C_6$cycloalkyl, $C_1$-$C_6$hydroxyalkyl, or $C_1$-$C_6$heteroalkyl;

$R^2$ is $C_1$-$C_6$alkoxy or hydroxy;

$R^3$ is $C_1$-$C_6$alkoxy or hydroxy;

or $R^2$ and $R^3$ are taken together with the carbon atom to which they are attached to form —C(═O)—, —C(═$NR^{13}$)—, —C(═N—$OR^{13}$)—, or a heterocyclic ring containing 2 O atoms;

$R^{13}$ is H or $C_1$-$C_6$alkyl;

$R^4$ is H, halogen, $C_1$-$C_6$alkyl, $C_1$-$C_6$fluoroalkyl, or $C_1$-$C_6$deuteroalkyl;

$R^5$ is H, halogen, $C_1$-$C_6$alkyl, $C_1$-$C_6$fluoroalkyl, or $C_1$-$C_6$deuteroalkyl;

or $R^4$ and $R^5$ are taken together with the carbon atom to which they are attached to form a substituted or unsubstituted $C_3$-$C_6$cycloalkyl ring, or a substituted or unsubstituted $C_3$-$C_6$heterocyclic ring containing 1 or 2 heteroatoms selected from —O—, —$NR^{12}$— and —S—;

$R^6$ is H, halogen, $C_1$-$C_6$alkyl, $C_1$-$C_6$fluoroalkyl, or $C_1$-$C_6$deuteroalkyl;

$R^7$ is H, halogen, $C_1$-$C_6$alkyl, $C_1$-$C_6$fluoroalkyl, or $C_1$-$C_6$deuteroalkyl;

or $R^6$ and $R^7$ are taken together with the carbon atom to which they are attached to form a substituted or unsubstituted $C_3$-$C_6$cycloalkyl ring, or a substituted or unsubstituted $C_3$-$C_6$heterocyclic ring containing 1 or 2 heteroatoms selected from —O—, —$NR^{12}$— and —S—;

$R^8$ is halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —CN, —$NO_2$, —OH, —$OR^{11}$, —$SR^{11}$, —S(═O)$R^{11}$, —S(═O)$_2R^{11}$, —S(═O)$_2$N($R^{12}$)$_2$, —$NR^{12}$S(═O)$_2R^{11}$, —C(═O)$R^{11}$, —OC(═O)$R^{11}$, —$CO_2R^{12}$, —$OCO_2R^{11}$, —N($R^{12}$)$_2$, —C(═O)N($R^{12}$)$_2$, —OC(═O)N($R^{12}$)$_2$, —NHC(═O)$R^{11}$, or —NHC(═O)$OR^{11}$;

$R^9$ is halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —CN, —$NO_2$, —OH, —$OR^{11}$, —$SR^{11}$, —S(═O)$R^{11}$, —S(═O)$_2R^{11}$, —S(═O)$_2$N($R^{12}$)$_2$, —$NR^{12}$S(═O)$_2R^{11}$, —C(═O)$R^{11}$, —OC(═O)$R^{11}$, —$CO_2R^{12}$, —$OCO_2R^{11}$, —N($R^{12}$)$_2$, —C(═O)N($R^{12}$)$_2$, —OC(═O)N($R^{12}$)$_2$, —NHC(═O)$R^{11}$, or —NHC(═O)$OR^{11}$; or each $R^{10}$ is independently H, halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —CN, —$NO_2$, —OH, —$OR^{11}$, —$SR^{11}$, —S(═O)$R^{11}$, —S(═O)$_2R^{11}$, —S(═O)$_2$N($R^{12}$)$_2$, —$NR^{12}$S(═O)$_2R^{11}$, —C(═O)$R^{11}$, —OC(═O)$R^{11}$, —$CO_2R^{12}$, —$OCO_2R^{11}$, —N($R^{12}$)$_2$, —C(═O)N($R^{12}$)$_2$, —OC(═O)N($R^{12}$)$_2$, —NHC(═O)$R^{11}$, or —NHC(═O)O$R^{11}$;

each $R^{11}$ is independently $C_1$-$C_6$alkyl, $C_1$-$C_6$fluoroalkyl, $C_1$-$C_6$deuteroalkyl, or $C_3$-$C_6$cycloalkyl;

each $R^{12}$ is independently H, $C_1$-$C_6$alkyl, $C_1$-$C_6$fluoroalkyl, $C_1$-$C_6$deuteroalkyl, or $C_3$-$C_6$cycloalkyl;

n is 0, 1, 2, or 3; and m is 0, 1, 2, or 3.

In some embodiments, each $R^1$ is independently H, halogen, $C_1$-$C_6$alkyl, $C_1$-$C_6$fluoroalkyl, $C_3$-$C_6$cycloalkyl. In some embodiments, each $R^1$ is independently H, F, Cl, Br, or $C_1$-$C_6$alkyl.

In some embodiments, $R^2$ and $R^3$ are taken together with the carbon atom to which they are attached to form —C(═O)—, —C(═N$R^{13}$)—, —C(═N—O$R^{13}$)—, or a heterocyclic ring containing 2 O atoms. In some embodiments, $R^2$ and $R^3$ are taken together with the carbon atom to which they are attached to form —C(═O)—, —C(═NH)—, —C(═N—OH)—, or

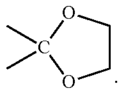

In some embodiments, $R^2$ and $R^3$ are taken together with the carbon atom to which they are attached to form —C(═O)—. In some embodiments, $R^{13}$ is H or $C_1$-$C_6$alkyl.

In some embodiments, $R^4$ is H, halogen, $C_1$-$C_6$alkyl, $C_1$-$C_6$fluoroalkyl, or $C_1$-$C_6$deuteroalkyl. In some embodiments, $R^4$ is H or $C_1$-$C_6$alkyl. In some embodiments, $R^4$ is H.

In some embodiments, $R^5$ is H, halogen, $C_1$-$C_6$alkyl, $C_1$-$C_6$fluoroalkyl, or $C_1$-$C_6$deuteroalkyl. In some embodiments, $R^5$ is H or $C_1$-$C_6$alkyl. In some embodiments, $R^5$ is H.

In some embodiments, $R^6$ is H, halogen, $C_1$-$C_6$alkyl, $C_1$-$C_6$fluoroalkyl, or $C_1$-$C_6$deuteroalkyl. In some embodiments, $R^6$ is H or $C_1$-$C_6$alkyl. In some embodiments, $R^6$ is H.

In some embodiments, $R^7$ is H, halogen, $C_1$-$C_6$alkyl, $C_1$-$C_6$fluoroalkyl, or $C_1$-$C_6$deuteroalkyl. In some embodiments, $R^7$ is H or $C_1$-$C_6$alkyl. In some embodiments, $R^7$ is H.

In some embodiments, $R^8$ is halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —OH, —O$R^{11}$, —S$R^{11}$, —S(═O)$R^{11}$, —S(═O)$_2R^{11}$, —C(═O)$R^{11}$, —CO$_2R^{12}$, —N($R^{12}$)$_2$, or —C(═O)N($R^{12}$)$_2$. In other embodiments, $R^8$ is F, Cl, Br, $C_1$-$C_6$alkyl, $C_1$-$C_6$fluoroalkyl, $C_1$-$C_6$cycloalkyl, $C_1$-$C_6$hydroxyalkyl, or $C_1$-$C_6$heteroalkyl.

In some embodiments, $R^9$ is halogen, $C_1$-$C_6$alkyl, $C_1$-$C_6$hydroxyalkyl, $C_1$-$C_6$heteroalkyl, —CN, —NO$_2$, —OH, —O$R^{11}$, —S$R^{11}$, —S(═O)$R^{11}$, —S(═O)$_2R^{11}$, —S(═O)$_2$N($R^{12}$)$_2$, —N$R^{12}$S(═O)$_2R^{11}$, —C(═O)$R^{11}$, —OC(═O)$R^{11}$, —CO$_2R^{12}$, —OCO$_2R^{11}$, —N($R^{12}$)$_2$, —C(═O)N($R^{12}$)$_2$, —OC(═O)N($R^{12}$)$_2$, —NHC(═O)$R^{11}$, or —NHC(═O)O$R^{11}$. In other embodiments, $R^9$ is F, Cl, Br, $C_1$-$C_6$alkyl, $C_1$-$C_6$hydroxyalkyl, $C_1$-$C_6$heteroalkyl, —OH, —O$R^{11}$, —S(═O)$_2R^{11}$, —S(═O)$_2$N($R^{12}$)$_2$, —N$R^{12}$S(═O)$_2R^{11}$, —C(═O)$R^{11}$, —CO$_2R^{12}$, —N($R^{12}$)$_2$, —C(═O)N($R^{12}$)$_2$, or —NHC(═O)$R^{11}$. In certain embodiments, $R^9$ is F, Cl, Br, $C_1$-$C_6$hydroxyalkyl, $C_1$-$C_6$heteroalkyl, —OH, or —O$R^{11}$, wherein $R^{11}$ is $C_1$-$C_6$alkyl.

In some embodiments, each $R^{10}$ is independently H, halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —OH, —O$R^{11}$, —S$R^{11}$, —S(═O)$R^{11}$, —S(═O)$_2R^{11}$, —C(═O)$R^{11}$, —CO$_2R^{12}$, —N($R^{12}$)$_2$, or —C(═O)N($R^{12}$)$_2$. In other embodiments, $R^{10}$ is F, Cl, Br, $C_1$-$C_6$alkyl, $C_1$-$C_6$fluoroalkyl, $C_1$-$C_6$cycloalkyl, $C_1$-$C_6$hydroxyalkyl, or $C_1$-$C_6$heteroalkyl.

In some embodiments, n is 2 or 3. In some embodiments, m is 1.

In one aspect, the compound of Formula (I), or a pharmaceutically acceptable salt, or solvate thereof, has the following structure of Formula (II):

Formula (II)

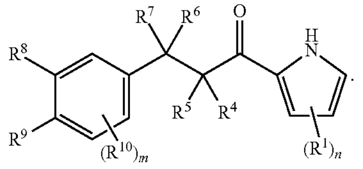

Any combination of the groups described above for the various variables is contemplated herein. Throughout the specification, groups and substituents thereof are chosen by one skilled in the field to provide stable moieties and compounds.

In one aspect, described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is in the form of a tablet, a pill, a capsule, a liquid, a suspension, a gel, a dispersion, a solution, an emulsion, an ointment, or a lotion.

In one aspect, described herein is a method of treating or preventing any one of the diseases or conditions described herein comprising administering a therapeutically effective amount of a compound described herein, or a pharmaceutically acceptable salt, or solvate thereof, to a mammal in need thereof.

In another aspect, described herein is a method for treating a $Ca^{2+}$ release-activated $Ca^{2+}$ (CRAC) channel-associated disease or disorder in a subject, comprising administering a therapeutically effective amount of a compound described herein, or a pharmaceutically acceptable salt, or solvate thereof, to the subject in need thereof. In some embodiments, the $Ca^{2+}$ release activated $Ca^{2+}$ (CRAC) channel-associated disease or disorder is an immune system-related disease or disorder involving inflammation, cancer or other proliferative disease, a hepatic disease or disorder, or a renal disease or disorder. In some embodiments, the $Ca^{2+}$ release activated $Ca^{2+}$ (CRAC) channel-associated disease or disorder is inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, allogeneic or xenogeneic transplantation, graft rejection, graft-versus-host disease, lupus erythematosus, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis, atopic dermatitis, asthma, Sjogren's syndrome, organ transplant rejection, multiple sclerosis, Guillain-Barre, autoimmune uveitis, autoimmune hemolytic anemia, pernicious anemia, autoimmune thrombocytopenia, temporal arteritis, anti-phospholipid syndrome, vasculitides such as Wegener's granulomatosis, Behcet's disease, psoriasis, dermatitis herpetiformis, pemphigus vulgaris, vitiligo, Crohn's disease, colitis, ulcerative colitis, primary biliary cirrhosis, autoimmune hepatitis, Type 1 or immune-mediated diabetes mellitus, Grave's disease, Hashimoto's thyroiditis, autoimmune oophoritis and orchitis, autoimmune disorder of the adrenal gland, systemic lupus erythematosus, polymyositis, dermatomyositis, ankylosing spondylitis, transplant rejection, skin graft rejection, arthritis, bone diseases associated with increased bone resorption, ileitis, Barrett's syndrome, adult respiratory distress syndrome, chronic obstructive airway disease; corneal dystrophy, trachoma, onchocerciasis, sympathetic ophthalmitis, endophthalmitis; gingivitis, periodontitis; tuberculosis; leprosy; uremic complications, nephrosis; sclerodermatitis, psoriasis, chronic demyelinating diseases of the nervous system, AIDS-related neurodegeneration, Alzheimer's disease, infectious meningitis, encephalomyelitis, Parkinson's disease, Huntington's disease, amyotrophic lateral sclerosis viral or autoimmune encephalitis; autoimmune disorders, immunecomplex vasculitis, systemic lupus and erythematodes; systemic lupus erythematosus (SLE); cardiomyopathy, ischemic heart disease hypercholesterolemia, atherosclerosis, preeclampsia; chronic liver failure, brain and spinal cord trauma, or cancer. In some embodiments, the $Ca^{2+}$ release activated $Ca^{2+}$ (CRAC) channel-associated disease or disorder is graft-versus-host disease.

Provided herein, in some embodiments, are methods for treating or preventing cancer in a subject, comprising administering a therapeutically effective amount of a compound described herein, or a pharmaceutically acceptable salt, or solvate thereof, to the subject in need thereof. In some embodiments, the cancer is a hematopoietic tumor of lymphoid lineage, leukemia, acute lymphocytic leukemia, acute lymphoblastic leukemia, B cell lymphoma, T-cell lymphoma, Hodgkin's lymphoma, non-Hodgkin's lymphoma, hairy cell lymphoma and Burkett's lymphoma; hematopoietic tumors of myeloid lineage, acute myelogenous leukemias, chronic myelogenous leukemias, myelodysplastic syndrome, promyelocytic leukemia; carcinoma of the bladder, carcinoma of the breast, carcinoma of the colon, carcinoma of the kidney, carcinoma of the liver, carcinoma of the lung, small cell lung cancer, esophageal cancer, gall bladder cancer, ovarian cancer, pancreatic cancer, stomach cancer, cervical cancer, thyroid cancer, prostate cancer, skin cancer, squamous cell carcinoma; tumors of mesenchymal origin, fibrosarcoma, rhabdomyosarcoma; tumors of the central and peripheral nervous system, astrocytoma, neuroblastoma, glioma, schwannoma; melanoma, seminoma, teratocarcinoma, osteosarcoma, xenoderoma pigmentosum, keratoctanthoma, thyroid follicular cancer, or Kaposi's sarcoma.

Provided herein, in some embodiments, are methods of reducing neuroinflammation in a subject in need thereof, comprising administering a therapeutically effective amount of a compound described herein, or a pharmaceutically acceptable salt, or solvate thereof, to the subject. In some embodiments, the subject has a neurological disease or disorder. In some embodiments, the subject has Alzheimer's disease, progressive multiple sclerosis, Huntington's disease, amyotrophic lateral sclerosis, or Parkinson's disease. In some embodiments, inflammation of microglia is reduced.

In any of the aforementioned aspects involving the treatment of $Ca^{2+}$ release activated $Ca^{2+}$ (CRAC) channel-associated diseases or disorders, are further embodiments comprising administering one or more additional therapeutic agents to the subject. In various embodiments, each agent is administered in any order, including simultaneously. In some embodiments, the additional therapeutic agent is an anti-inflammatory agent, anti-cancer agent immunosuppressive agent, steroid, non-steroidal anti-inflammatory agent, antihistamine, or analgesic.

In any of the aforementioned aspects are further embodiments in which the effective amount of the compound described herein, or a pharmaceutically acceptable salt thereof, is: systemically administered to the subject; and/or administered orally to the subject; and/or intravenously administered to the subject; and/or administered by inhalation; and/or administered by nasal administration; or and/or administered by injection to the subject; and/or administered topically to the subject; and/or administered by ophthalmic administration; and/or administered rectally to the subject; and/or administered non-systemically or locally to the subject.

In any of the aforementioned aspects are further embodiments comprising single administrations of the effective amount of the compound, including further embodiments in which the compound is administered once a day to the subject or the compound is administered to the subject multiple times over the span of one day. In some embodiments, the compound is administered on a continuous dosing schedule. In some embodiments, the compound is administered on a continuous daily dosing schedule.

In any of the embodiments disclosed herein, the subject is a mammal. In any of the embodiments disclosed herein, the mammal is a human. In some embodiments, compounds provided herein are administered to a human.

Articles of manufacture, which include packaging material, a compound described herein, or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for inhibiting the activity of CRAC channels, or for the treatment, prevention or amelioration of one or more symptoms of a disease or condition that would benefit from inhibition of the activity of CRAC channels, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

CRAC and Orai

Figure 1:
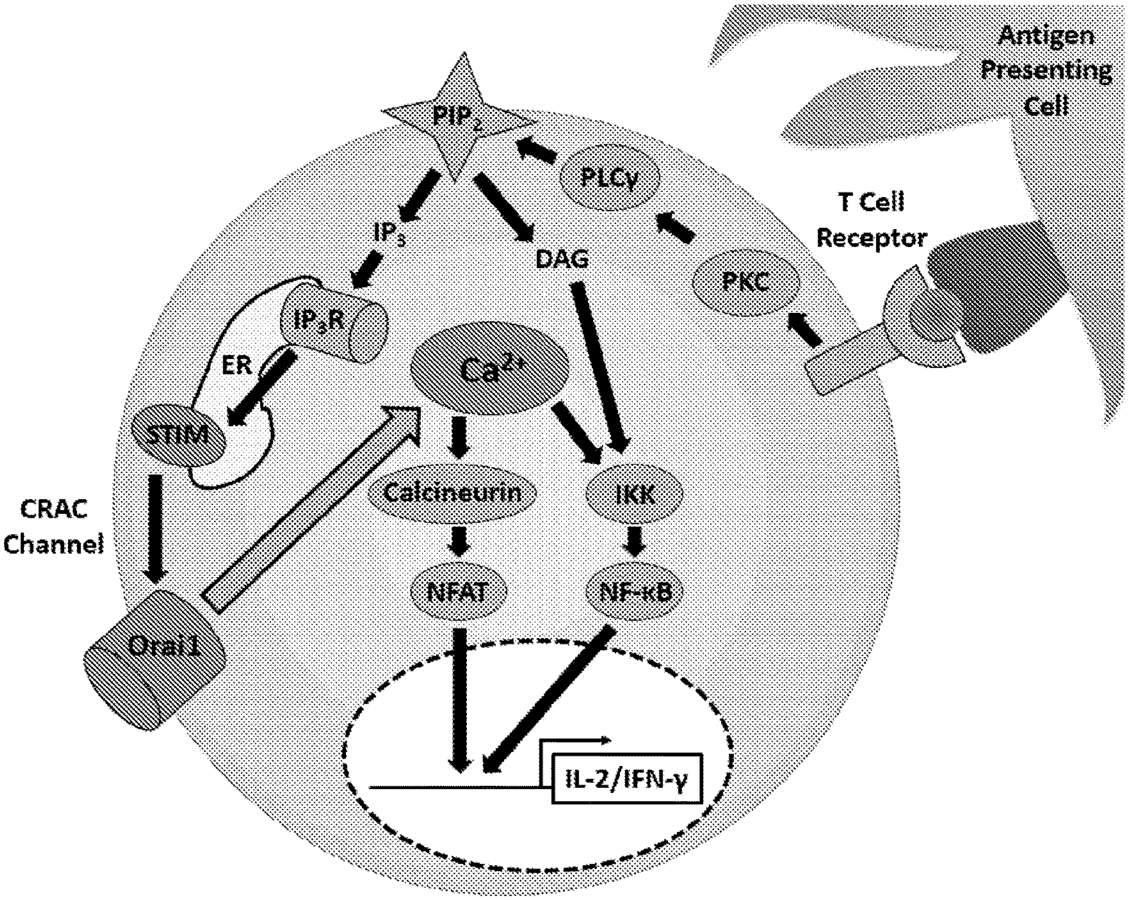
FIG. 1 depicts $Ca^{2+}$ signaling cascades in T cells.

CRAC channels are essential for the proper function of many cells, including T cells. CRAC channel opening creates a favorable electrochemical environment for $Ca^{2+}$ ions to flow along their concentration gradient into the cytoplasm of a cell. $Ca^{2+}$ entry through CRAC channels drives exocytosis, stimulates mitochondrial metabolism, activates gene expression, promotes cell growth and proliferation, activates integrins, enables cytokine production, and facilitates histamine release. CRAC channel activation occurs following engagement of receptors on the plasma membrane, including T cell receptors, B cell receptors, and G-protein coupled receptors. $Ca^{2+}$ acts as an important intracellular second messenger, enabling activation of multiple $Ca^{2+}$-dependent signaling and transcription factor proteins, including nuclear factor kappa-light-chain-enhancer of activated B cells (NF-κB) and nuclear factor of activated T cells (NFAT).

Some embodiments provided herein describe a method of modulating store-operated $Ca^{2+}$ (SOC) channel activity, the method comprising contacting the SOC channel complex, or portion thereof with a compound by administering an effective amount of a compound of Formula (I); or pharmaceutically acceptable salt, pharmaceutically acceptable solvate, or pharmaceutically acceptable prodrug thereof, described herein, comprising administering a therapeutically effective amount of a compound described herein, or a pharmaceutically acceptable salt, or solvate thereof, to a mammal in need thereof. In some embodiments, the contacting occurs in vitro. In other embodiments, the contacting occurs in vivo.

Also provided herein, in some embodiments, are methods of modulating $Ca^{2+}$ release activated $Ca^{2+}$ channel (CRAC) activity in a mammal comprising administering to the mammal a compound of Formula (I), wherein the compound of Formula (I) modulates CRAC activity in the mammal. In some embodiments, the compound of Formula (I) interacts with the stromal interaction molecules, STIM1 and/or STIM2. In some embodiments, the compound of Formula (I) alters the expression or physiological function of the stromal interaction molecules, STIM1 and/or STIM2. In some embodiments, the compound of Formula (I) interacts with Orai $Ca^{2+}$ channel molecules, Orai1, Orai2, and/or Orai3. In some embodiments, the compound of Formula (I) alters the expression or physiological function Orai $Ca^{2+}$ channel molecules, Orai1, Orai2, and/or Orai3. In some embodiments, modulating $Ca^{2+}$ release activated $Ca^{2+}$ (CRAC) channel function with a compound of Formula (I) inhibits the electrophysiological current $I_{CRAC}$ associated with activation of CRAC channels.

Other embodiments provided herein describe methods of inhibiting store-operated $Ca^{2+}$ entry (SOCE) activation of nuclear factor of activated T cells (NF-AT) in a mammal comprising administering to the mammal a compound of Formula (I), wherein the compound of Formula (I) inhibits SOCE activation of NF-AT in the mammal. Other embodiments provided herein describe methods of inhibiting store-operated $Ca^{2+}$ entry (SOCE) activation of NF-κB (nuclear factor kappa-light-chain-enhancer of activated B cells) in a mammal comprising administering to the mammal a compound of Formula (I), wherein the compound of Formula (I) inhibits SOCE activation of NF-κB in the mammal.

Also provided herein are methods of decreasing cytokine release by inhibiting the SOCE-mediated activation of NF-AT in a mammal, the method comprising administering to the mammal a compound of Formula (I), wherein the compound of Formula (I) decreases cytokine release in the mammal. Some embodiments provided herein describe methods of decreasing cytokine release by inhibiting the SOCE-mediated activation of NF-κB in a mammal, the method comprising administering to the mammal a compound of Formula (I), wherein the compound of Formula (I) decreases cytokine release in the mammal.

In some embodiments, a compound of Formula (I) inhibits cytokine production in a cell. In some embodiments, the cytokine is an interleukin, interferon, transforming growth factor, tumor necrosis factor, colony stimulating factor, or combinations thereof. In some embodiments, a method of inhibiting chemokine production in a cell is described, the method comprising administering to the cell a compound of Formula (I). Also described is a method of inhibiting immune cell activation, the method comprising administering to the immune cell a compound of Formula (I).

Also provided herein are methods of polarizing immune cells to regulatory phenotypes, the method comprising administering to the immune cell a compound of Formula (I).

Some embodiments provided herein describe methods of inducing forkhead box P3 (Foxp3) production in a cell, the method comprising administering to the cell a compound of Formula (I).

Other embodiments provided herein describe methods of increasing anti-inflammatory cytokines in a mammal by generating regulatory immune cell subsets, the method comprising administering to the mammal a compound of Formula (I). In some embodiments, the anti-inflammatory cytokine is IL-2, IL-4, IL-10, TGF-β, or combinations thereof.

Some embodiments provided herein describe methods of inhibiting cell proliferation in response to an antigen, the method comprising administering to the cell a compound of Formula (I).

Also provided herein are methods of modulating an ion channel in a cell, wherein the ion channel is involved in immune cell activation, comprising administering to the cell a compound of Formula (I). In some embodiments, the immune cell that mediates disease is a T cell, B cell, dendritic cell, macrophage, monocyte, mast cell, neutrophil, eosinophil, or combinations thereof.

Diseases or Disorders

In some instances, inhibition of CRAC channel function is effective in preventing pro-inflammatory immune function and/or enhancing anti-inflammatory responses. In some instances, a cell activated through the Orai1 $Ca^{2+}$ signaling cascade produces a variety of chemokines and cytokines. Chemokines and cytokines mediate a wide range of physiological processes at the site of production and throughout the body. Certain chemokines and cytokines mediate normal cellular function during homeostasis, others provide protection during infection or following tissue damage, and others mediate the immunopathogenesis of a number of pathologies.

Cytokines encompass a variety of protein families including interleukins, interferons, transforming growth factors, tumor necrosis factors, and colony stimulating factors. Each cytokine or chemokine mediates a specific physiological response to external stimuli including cancer, pathogens, and toxins. Cytokine and chemokine producing cells include, but are not limited to endothelial cells, fibroblasts, stromal cells, and cells of the immune system including mast cells, basophils, neutrophils, eosinophils, monocytes, macrophages, natural killer cells, dendritic cells, T cells, B cells, and plasma cells.

Some embodiments provided herein describe methods for the treatment of $Ca^{2+}$ release-activated $Ca^{2+}$ (CRAC) channel-associated diseases or disorders, the method comprising administering to a subject in need thereof an effective amount of a compound of Formula (I).

In some embodiments, the $Ca^{2+}$ release activated $Ca^{2+}$ (CRAC) channel-associated disease or disorder is an immune system-related disease or disorder involving inflammation, cancer or other proliferative disease, a hepatic disease or disorder, or a renal disease or disorder. CRAC channel-associated diseases or disorders include, but are not limited to: inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, allogeneic or xenogeneic transplantation, graft rejection, graft-versus-host disease, lupus erythematosus, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis, atopic dermatitis, asthma, Sjogren's syndrome, organ transplant rejection, multiple sclerosis, Guillain-Barre, autoimmune uveitis, autoimmune hemolytic anemia, pernicious anemia, autoimmune thrombocytopenia, temporal arteritis, anti-phospholipid syndrome, vasculitides such as Wegener's granulomatosis, Behcet's disease, psoriasis, dermatitis herpetiformis, pemphigus vulgaris, vitiligo, Crohn's disease, colitis, ulcerative colitis, primary biliary cirrhosis, autoimmune hepatitis, Type 1 or immune-mediated diabetes mellitus, Grave's disease, Hashimoto's thyroiditis, autoimmune oophoritis and orchitis, autoimmune disorder of the adrenal gland, systemic lupus erythematosus, polymyositis, dermatomyositis, ankylosing spondylitis, transplant rejection, skin graft rejection, arthritis, bone diseases associated with increased bone resorption, ileitis, Barrett's syndrome, adult respiratory distress syndrome, chronic obstructive airway disease; comeal dystrophy, trachoma, onchocerciasis, sympathetic ophthalmitis, endophthalmitis; gingivitis, periodontitis; tuberculosis; leprosy; uremic complications, nephrosis; sclerodermatitis, psoriasis, chronic demyelinating diseases of the nervous system, AIDS-related neurodegeneration, Alzheimer's disease, infectious meningitis, encephalomyelitis, Parkinson's disease, Huntington's disease, amyotrophic lateral sclerosis viral or autoimmune encephalitis; autoimmune disorders, immunecomplex vasculitis, systemic lupus and erythematodes; systemic lupus erythematosus (SLE); cardiomyopathy, ischemic heart disease hypercholesterolemia, atherosclerosis, preeclampsia; chronic liver failure, brain and spinal cord trauma, and cancer.

In some embodiments, the $Ca^{2+}$ release activated $Ca^{2+}$ (CRAC) channel-associated disease or disorder is transplant rejection, including skin graft rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including comeal dystrophy, trachoma, onchocerciasis, uveitis, sympathetic ophthalmitis and endophthalmitis; chronic inflammatory disorders of the gums, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune disorders, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis; as well as various other diseases with significant inflammatory components, including preeclampsia; chronic liver failure, brain and spinal cord trauma, or cancer.

In some embodiments, the $Ca^{2+}$ release activated $Ca^{2+}$ (CRAC) channel-associated disease or disorder is glomerulonephritis, uveitis, hepatic diseases or disorders, renal diseases or disorders, chronic obstructive pulmonary disease, vasculitis, osteoarthritis, inflammatory muscle disease, allergic rhinitis, vaginitis, interstitial cystitis, scleroderma, osteoporosis, eczema, allogeneic or xenogeneic transplantation, graft-versus-host disease, type I diabetes, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis, atopic dermatitis, Sjogren's syndrome, cancer and other proliferative diseases, chronic obstructive pulmonary disease, allergic rhinitis, or Grave's disease. In some embodiments, the $Ca^{2+}$ release activated $Ca^{2+}$ (CRAC) channel-associated disease or disorder is graft-versus-host disease.

In some embodiments, the $Ca^{2+}$ release activated $Ca^{2+}$ (CRAC) channel-associated disease or disorder is an autoimmune disorder. In certain embodiments, the autoimmune disease is chronic obstructive pulmonary disease, rheumatoid arthritis, inflammatory bowel disease, allergic rhinitis, asthma, multiple sclerosis, psoriasis, Crohn's disease, colitis, ulcerative colitis, arthritis, bone diseases associated with increased bone resorption, rheumatoid arthritis, Sjorgen, Graves, ITP, asthma, or chronic obstructive airway disease. In some embodiments, the $Ca^{2+}$ release activated $Ca^{2+}$ (CRAC) channel-associated disease or disorder is multiple sclerosis. In certain embodiments, the $Ca^{2+}$ release activated $Ca^{2+}$ (CRAC) channel-associated disease or disorder is inflammatory bowel disease.

Also provided herein are methods of suppressing the immune system of a subject in need thereof, the method comprising administering to the subject an effective amount of a compound of Formula (I). Some embodiments provided herein describe the treatment or prevention of an allergic disorder in a subject in need thereof, the method comprising administering to the subject an effective amount of a compound of Formula (I). In some embodiments, the allergic disorder is allergic rhinitis, sinusitis, rhinosinusitis, chronic otitis media, recurrent otitis media, drug reactions, insect sting reactions, latex reactions, conjunctivitis, urtic aria, anaphylaxis reactions, anaphylactoid reactions, atopic dermatitis, asthma, or food allergies.

In some instances, Orai and STIM proteins facilitate cancer cell proliferation, growth, migration, and metastasis. In some instances, Orai protein activity, STIM protein activity, and $Ca^{2+}$ influx are required for mammary tumor metastasis.

In some instances, Orai proteins inhibit caspase-induced cell death in tumor cells. A combination of caspase proteins, Fas-associated death domain proteins, and CD95 proteins form an apoptosis-inducing signaling complex in mammalian cells. Apoptosis is a programmed cell-death pathway that is essential for preventing tumor development. In some instances, Orai1 proteins interact with this signaling complex to mediate $Ca^{2+}$ influx and prevent apoptosis in cancer cells.

Provided herein are methods of regulating tumor or cancer cell growth, migration, and/or metastasis. In some embodiments, disclosed herein are methods of treating cancer with a compound disclosed herein.

The term "cancer" as used herein, refers to an abnormal growth of cells that tend to proliferate in an uncontrolled way and, in some cases, to metastasize (spread). Types of cancer include, but are not limited to, solid tumors (such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer) and hematological tumors (such as the leukemias and lymphomas) at any stage of the disease with or without metastases. In some embodiments, cancer is a hematopoietic tumor of lymphoid lineage, leukemia, acute lymphocytic leukemia, acute lymphoblastic leukemia, B cell lymphoma, T-cell lymphoma, Hodgkin's lymphoma, non-Hodgkin's lymphoma, hairy cell lymphoma and Burkett's lymphoma; hematopoietic tumors of myeloid lineage, acute myelogenous leukemias, chronic myelogenous leukemias, myelodysplastic syndrome, promyelocytic leukemia; carcinoma of the bladder, carcinoma of the breast, carcinoma of the colon, carcinoma of the kidney, carcinoma of the liver, carcinoma of the lung, small cell lung cancer, esophageal cancer, gall bladder cancer, ovarian cancer, pancreatic cancer, stomach cancer, cervical cancer, thyroid cancer, prostate cancer, skin cancer, squamous cell carcinoma; tumors of mesenchymal origin, fibrosarcoma, rhabdomyosarcoma; tumors of the central and peripheral nervous system, astrocytoma, neuroblastoma, glioma, schwannoma; melanoma, seminoma, teratocarcinoma, osteosarcoma, xenoderoma pigmentosum, keratoctanthoma, thyroid follicular cancer, or Kaposi's sarcoma. In some embodiments, the cancer is large cell lung cancer or acute lymphoblastic leukemia. In certain embodiments, the cancer is large cell lung cancer. In certain embodiments, the cancer is acute lymphoblastic leukemia.

Some embodiments provided herein describe methods of treating microglial-associated diseases or disorders with a compound disclosed herein. Microglia express the Orai1 and STIM1 proteins essential for CRAC channel function. Microglia also have thapsigargin-induced $I_{CRAC}$ and a number of inflammatory pathways that rely on CRAC channel function. In some instances, microglia priming and the subsequent inflammatory response lead to exacerbated tissue damage in animal models of prion disease, Alzheimer's disease, Parkinson's disease, stroke and multiple sclerosis. In some instances, age-related activation of microglial cells within the hypothalamus contributes to the relationships between chronic systemic inflammatory conditions, such as atherosclerosis, obesity and diabetes, and the development of age-related neurodegenerative disease. Further, in some instances, severe systemic inflammation, such as sepsis, affects the microglial phenotype. In some embodiments, the microglial-associated disease or disorder to be treated is prion disease, Alzheimer's disease, Parkinson's disease, stroke, traumatic brain injury, multiple sclerosis, atherosclerosis, obesity, diabetes, aging, or sepsis. In some embodiments, the microglial-associated disease or disorder to be treated is prion disease, Alzheimer's disease, Parkinson's disease, stroke, multiple sclerosis, atherosclerosis, obesity, diabetes, or sepsis. In some embodiments, the microglial-associated disease or disorder to be treated is stroke, traumatic brain injury, Alzheimer's disease, or ALS. In some embodiments, the microglial-associated disease or disorder is prion disease. In some embodiments, the microglial-associated disease or disorder is Parkinson's disease. In some embodiments, the microglial-associated disease or disorder is stroke. In some embodiments, the microglial-associated disease or disorder is traumatic brain injury. In some embodiments, the microglial-associated disease or disorder is multiple sclerosis. In some embodiments, the microglial-associated disease or disorder is atherosclerosis. In certain embodiments, the microglial-associated disease or disorder is sepsis. In certain embodiments, the microglial-associated disease or disorder is Alzheimer's disease. In certain embodiments, the microglial-associated disease or disorder is ALS. In some embodiments, the microglial-associated disease or disorder is obesity, obesity-related diabetes, or aging.

Compounds

Compounds described herein, including pharmaceutically acceptable salts, prodrugs, active metabolites and pharmaceutically acceptable solvates thereof, are CRAC channel inhibitors.

In one aspect, described herein is a compound of Formula (I), or a pharmaceutically acceptable salt, or solvate thereof:

Formula (I)

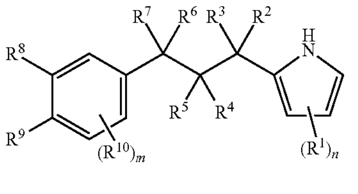

wherein, each $R^1$ is independently H, halogen, $C_1$-$C_6$alkyl, $C_1$-$C_6$fluoroalkyl, $C_1$-$C_6$deuteroalkyl, $C_3$-$C_6$cycloalkyl, $C_1$-$C_6$hydroxyalkyl, or $C_1$-$C_6$heteroalkyl;

$R^2$ is $C_1$-$C_6$alkoxy or hydroxy;

$R^3$ is $C_1$-$C_6$alkoxy or hydroxy;

or $R^2$ and $R^3$ are taken together with the carbon atom to which they are attached to form —C(═O)—, —C(═$NR^{13}$)—, —C(═N—$OR^{13}$)—, or a heterocyclic ring containing 2 O atoms;

$R^{13}$ is H or $C_1$-$C_6$alkyl;

$R^4$ is H, halogen, $C_1$-$C_6$alkyl, $C_1$-$C_6$fluoroalkyl, or $C_1$-$C_6$deuteroalkyl;

$R^5$ is H, halogen, $C_1$-$C_6$alkyl, $C_1$-$C_6$fluoroalkyl, or $C_1$-$C_6$deuteroalkyl;

or $R^4$ and $R^5$ are taken together with the carbon atom to which they are attached to form a substituted or unsubstituted $C_3$-$C_6$cycloalkyl ring, or a substituted or unsubstituted $C_3$-$C_6$heterocyclic ring containing 1 or 2 heteroatoms selected from —O—, —$NR^{12}$— and —S—;

$R^6$ is H, halogen, $C_1$-$C_6$alkyl, $C_1$-$C_6$fluoroalkyl, or $C_1$-$C_6$deuteroalkyl;

$R^7$ is H, halogen, $C_1$-$C_6$alkyl, $C_1$-$C_6$fluoroalkyl, or $C_1$-$C_6$deuteroalkyl;

or $R^6$ and $R^7$ are taken together with the carbon atom to which they are attached to form a substituted or unsubstituted $C_3$-$C_6$cycloalkyl ring, or a substituted or unsubstituted $C_3$-$C_6$heterocyclic ring containing 1 or 2 heteroatoms selected from —O—, —$NR^{12}$— and —S—;

$R^8$ is H, halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —CN, —$NO_2$, —OH, —$OR^{11}$, —$SR^{11}$, —S(═O)$R^{11}$, —S(═O)$_2R^{11}$, —S(═O)$_2$N($R^{12}$)$_2$, —$NR^{12}$S(═O)$_2R^{11}$, —C(═O)$R^{11}$, —OC(═O)$R^{11}$, —$CO_2R^{12}$, —$OCO_2R^{11}$, —N($R^{12}$)$_2$, —C(═O)N($R^{12}$)$_2$, —OC(═O)N($R^{12}$)$_2$, —NHC(═O)$R^{11}$, or —NHC(═O)$OR^{11}$;

$R^9$ is H, halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —CN, —$NO_2$, —OH, —$OR^{11}$, —$SR^{11}$, —S(═O)$R^{11}$, —S(═O)$_2R^{11}$, —S(═O)$_2$N($R^{12}$)$_2$, —$NR^{12}$S(═O)$_2R^{11}$, —C(═O)$R^{11}$, —OC(═O)$R^{11}$, —$CO_2R^{12}$, —$OCO_2R^{11}$, —N($R^{12}$)$_2$, —C(═O)N($R^{12}$)$_2$, —OC(═O)N($R^{12}$)$_2$, —NHC(═O)$R^{11}$, or —NHC(═O)$OR^{11}$; or each $R^{10}$ is independently H, halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —CN, —$NO_2$, —OH, —$OR^{11}$, —$SR^{11}$, —S(═O)$R^{11}$, —S(═O)$_2R^{11}$, —S(═O)$_2$N($R^{12}$)$_2$, —$NR^{12}$S(═O)$_2R^{11}$, —C(═O)$R^{11}$, —OC(═O)$R^{11}$, —$CO_2R^{12}$, —$OCO_2R^{11}$, —N($R^{12}$)$_2$, —C(═O)N($R^{12}$)$_2$, —OC(═O)N($R^{12}$)$_2$, —NHC(═O)$R^{11}$, or —NHC(═O)$OR^{11}$;

each $R^{11}$ is independently $C_1$-$C_6$alkyl, $C_1$-$C_6$fluoroalkyl, $C_1$-$C_6$deuteroalkyl, or $C_3$-$C_6$cycloalkyl;

each $R^{12}$ is independently H, $C_1$-$C_6$alkyl, $C_1$-$C_6$fluoroalkyl, $C_1$-$C_6$deuteroalkyl, or $C_3$-$C_6$cycloalkyl;

n is 0, 1, 2, or 3; and m is 0, 1, 2, or 3.

In one aspect, described herein is a compound of Formula (I), or a pharmaceutically acceptable salt, or solvate thereof:

Formula (I)

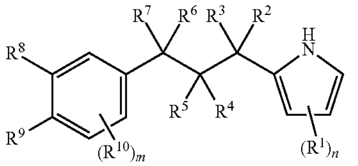

wherein, each $R^1$ is independently H, halogen, $C_1$-$C_6$alkyl, $C_1$-$C_6$fluoroalkyl, $C_1$-$C_6$deuteroalkyl, $C_3$-$C_6$cycloalkyl, $C_1$-$C_6$hydroxyalkyl, or $C_1$-$C_6$heteroalkyl;

$R^2$ is $C_1$-$C_6$alkoxy or hydroxy;

$R^3$ is $C_1$-$C_6$alkoxy or hydroxy;

or $R^2$ and $R^3$ are taken together with the carbon atom to which they are attached to form —C(═O)—, —C(═$NR^{13}$)—, —C(═N—$OR^{13}$)—, or a heterocyclic ring containing 2 O atoms;

$R^{13}$ is H or $C_1$-$C_6$alkyl;

$R^4$ is H, halogen, $C_1$-$C_6$alkyl, $C_1$-$C_6$fluoroalkyl, or $C_1$-$C_6$deuteroalkyl;

$R^5$ is H, halogen, $C_1$-$C_6$alkyl, $C_1$-$C_6$fluoroalkyl, or $C_1$-$C_6$deuteroalkyl;

or $R^4$ and $R^5$ are taken together with the carbon atom to which they are attached to form a substituted or unsubstituted $C_3$-$C_6$cycloalkyl ring, or a substituted or unsubstituted $C_3$-$C_6$heterocyclic ring containing 1 or 2 heteroatoms selected from —O—, —$NR^{12}$— and —S—;

$R^6$ is H, halogen, $C_1$-$C_6$alkyl, $C_1$-$C_6$fluoroalkyl, or $C_1$-$C_6$deuteroalkyl;

$R^7$ is H, halogen, $C_1$-$C_6$alkyl, $C_1$-$C_6$fluoroalkyl, or $C_1$-$C_6$deuteroalkyl;

or $R^6$ and $R^7$ are taken together with the carbon atom to which they are attached to form a substituted or unsubstituted $C_3$-$C_6$cycloalkyl ring, or a substituted or unsubstituted $C_3$-$C_6$heterocyclic ring containing 1 or 2 heteroatoms selected from —O—, —$NR^{12}$— and —S—;

$R^8$ is halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —CN, —$NO_2$, —OH, —$OR^{11}$, —$SR^{11}$, —S(═O)$R^{11}$, —S(═O)$_2R^{11}$, —S(═O)$_2$N($R^{12}$)$_2$, —$NR^{12}$S(═O)$_2R^{11}$, —C(═O)$R^{11}$, —OC(═O)$R^{11}$, —$CO_2R^{12}$, —$OCO_2R^{11}$, —N($R^{12}$)$_2$, —C(═O)N($R^{12}$)$_2$, —OC(═O)N($R^{12}$)$_2$, —NHC(═O)$R^{11}$, or —NHC(═O)$OR^{11}$;

$R^9$ is halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —CN, —$NO_2$, —OH, —$OR^{11}$, —$SR^{11}$, —S(═O)$R^{11}$, —S(═O)$_2R^{11}$, —S(═O)$_2$N($R^{12}$)$_2$, —$NR^{12}$S(═O)$_2R^{11}$, —C(═O)$R^{11}$, —OC(═O)$R^{11}$, —$CO_2R^{12}$, —$OCO_2R^{11}$, —N($R^{12}$)$_2$, —C(═O)N($R^{12}$)$_2$, —OC(═O)N($R^{12}$)$_2$, —NHC(═O)$R^{11}$, or —NHC(═O)$OR^{11}$; or each $R^{10}$ is independently H, halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —CN, —$NO_2$, —OH, —$OR^{11}$, —$SR^{11}$, —S(═O)$R^{11}$, —S(═O)$_2R^{11}$, —S(═O)$_2$N($R^{12}$)$_2$, —$NR^{12}$S(═O)$_2R^{11}$, —C(═O)$R^{11}$, —OC(═O)$R^{11}$, —$CO_2R^{12}$, —$OCO_2R^{11}$, —N($R^{12}$)$_2$, —C(═O)N($R^{12}$)$_2$, —OC(═O)N($R^{12}$)$_2$, —NHC(═O)$R^{11}$, or —NHC(═O)$OR^{11}$;

each $R^{11}$ is independently $C_1$-$C_6$alkyl, $C_1$-$C_6$fluoroalkyl, $C_1$-$C_6$deuteroalkyl, or $C_3$-$C_6$cycloalkyl;

each $R^{12}$ is independently H, $C_1$-$C_6$alkyl, $C_1$-$C_6$fluoroalkyl, $C_1$-$C_6$deuteroalkyl, or $C_3$-$C_6$cycloalkyl;

n is 0, 1, 2, or 3; and m is 0, 1, 2, or 3.

In some embodiments, each $R^1$ is independently H, halogen, $C_1$-$C_3$alkyl, $C_1$-$C_3$fluoroalkyl, $C_1$-$C_3$deuteroalkyl, $C_3$-$C_4$cycloalkyl, $C_1$-$C_3$hydroxyalkyl, or $C_1$-$C_3$heteroalkyl. In some embodiments, each $R^1$ is independently H, halogen, $C_1$-$C_6$alkyl, $C_1$-$C_6$fluoroalkyl, or $C_3$-$C_6$cycloalkyl. In some embodiments, each $R^1$ is independently H, halogen, $C_1$-$C_3$alkyl, $C_1$-$C_3$fluoroalkyl, or $C_3$-$C_4$cycloalkyl. In some embodiments, each $R^1$ is independently H, F, Cl, Br, or $C_1$-$C_6$alkyl. In some embodiments, each $R^1$ is independently H, F, Cl, Br, or $C_1$-$C_3$alkyl. In some embodiments, each $R^1$ is independently H, F, Cl, Br, methyl, ethyl, propyl, iso-propyl, n-butyl, iso-butyl, sec-butyl, or t-butyl. In some embodiments, each $R^1$ is independently H, F, Cl, Br, methyl, ethyl, propyl, iso-propyl, or t-butyl. In some embodiments, each $R^1$ is independently H, F, Cl, Br, methyl, ethyl, propyl, iso-propyl, or t-butyl. In some embodiments, each $R^1$ is independently H, F, Cl, or Br. In some embodiments, each $R^1$ is independently F, Cl, or Br. In certain embodiments, at least one $R^1$ is Cl. In certain embodiments, at least two $R^1$ are Cl. In some embodiments, each $R^1$ is H.

In some embodiments, $R^2$ and $R^3$ are taken together with the carbon atom to which they are attached to form —C(═O)—, —C(═$NR^{13}$)—, —C(═N—$OR^{13}$)—, or a heterocyclic ring containing 2 O atoms. In some embodiments, $R^2$ and $R^3$ are taken together with the carbon atom to which they are attached to form —C(═O)—, —C(═NH)—, —C(═N—OH)—, or

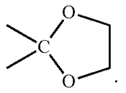

In some embodiments, $R^2$ and $R^3$ are taken together with the carbon atom to which they are attached to form —C(═O)—. In some embodiments, $R^2$ and $R^3$ are taken together with the carbon atom to which they are attached to form —C(═NH)—. In some embodiments, $R^2$ and $R^3$ are taken together with the carbon atom to which they are attached to form —C(═N—OH)—. In some embodiments, $R^2$ and $R^3$ are taken together with the carbon atom to which they are attached to form

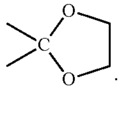

In some embodiments, $R^{13}$ is H or $C_1$-$C_6$alkyl. In some embodiments, $R^{13}$ is H, methyl, ethyl.

In some embodiments, $R^2$ and $R^3$ are $C_1$-$C_6$alkoxy. In some embodiments, $R^2$ and $R^3$ are methoxy or ethoxy. In some embodiments, $R^2$ is $C_1$-$C_6$alkoxy and $R^3$ is hydroxy. In some embodiments, $R^2$ is methoxy or ethoxy and $R^3$ is hydroxy.

In some embodiments, $R^4$ is H, halogen, $C_1$-$C_6$alkyl, $C_1$-$C_6$fluoroalkyl, or $C_1$-$C_6$deuteroalkyl. In some embodiments, $R^4$ is H, halogen, $C_1$-$C_3$alkyl, $C_1$-$C_3$fluoroalkyl, or $C_1$-$C_3$deuteroalkyl. In some embodiments, $R^4$ is H or $C_1$-$C_6$alkyl. In some embodiments, $R^4$ is H or $C_1$-$C_3$alkyl. In some embodiments, $R^4$ is H, methyl, ethyl, propyl, or iso-propyl. In some embodiments, $R^4$ is H or methyl. In some embodiments, $R^4$ is $C_1$-$C_6$alkyl. In some embodiments, $R^4$ is $C_1$-$C_3$alkyl. In some embodiments, $R^4$ is H.

In some embodiments, $R^5$ is H, halogen, $C_1$-$C_6$alkyl, $C_1$-$C_6$fluoroalkyl, or $C_1$-$C_6$deuteroalkyl. In some embodiments, $R^5$ is H, halogen, $C_1$-$C_3$alkyl, $C_1$-$C_3$fluoroalkyl, or $C_1$-$C_3$deuteroalkyl. In some embodiments, $R^5$ is H or $C_1$-$C_6$alkyl. In some embodiments, $R^5$ is H or $C_1$-$C_3$alkyl. In some embodiments, $R^5$ is H, methyl, ethyl, propyl, or iso-propyl. In some embodiments, $R^5$ is H or methyl. In some embodiments, $R^5$ is $C_1$-$C_6$alkyl. In some embodiments, $R^5$ is $C_1$-$C_3$alkyl. In some embodiments, $R^5$ is H.

In some embodiments, $R^4$ and $R^5$ are taken together with the carbon atom to which they are attached to form a substituted or unsubstituted $C_3$-$C_6$cycloalkyl ring, or a substituted or unsubstituted $C_3$-$C_6$heterocyclic ring containing 1 or 2 heteroatoms selected from —O—, —$NR^{12}$— and —S—. In some embodiments, $R^4$ and $R^5$ are taken together with the carbon atom to which they are attached to form a substituted or unsubstituted $C_3$-$C_6$cycloalkyl ring. In some embodiments, $R^4$ and $R^5$ are taken together with the carbon atom to which they are attached to form a cyclopropyl ring. In some embodiments, $R^4$ and $R^5$ are taken together with the carbon atom to which they are attached to form a substituted or unsubstituted $C_3$-$C_6$heterocyclic ring containing 1 or 2 heteroatoms selected from —O—, —$NR^{12}$— and —S—.

In some embodiments, $R^6$ is H, halogen, $C_1$-$C_6$alkyl, $C_1$-$C_6$fluoroalkyl, or $C_1$-$C_6$deuteroalkyl. In some embodiments, $R^6$ is H, halogen, $C_1$-$C_3$alkyl, $C_1$-$C_3$fluoroalkyl, or $C_1$-$C_3$deuteroalkyl. In some embodiments, $R^6$ is H or $C_1$-$C_6$alkyl. In some embodiments, $R^6$ is H or $C_1$-$C_3$alkyl. In some embodiments, $R^6$ is H, methyl, ethyl, propyl, or iso-propyl. In some embodiments, $R^6$ is H or methyl. In some embodiments, $R^6$ is $C_1$-$C_6$alkyl. In some embodiments, $R^6$ is $C_1$-$C_3$alkyl. In some embodiments, $R^6$ is H.

In some embodiments, $R^7$ is H, halogen, $C_1$-$C_6$alkyl, $C_1$-$C_6$fluoroalkyl, or $C_1$-$C_6$deuteroalkyl. In some embodiments, $R^7$ is H, halogen, $C_1$-$C_3$alkyl, $C_1$-$C_3$fluoroalkyl, or $C_1$-$C_3$deuteroalkyl. In some embodiments, $R^7$ is H or $C_1$-$C_6$alkyl. In some embodiments, $R^7$ is H or $C_1$-$C_3$alkyl. In some embodiments, $R^7$ is H, methyl, ethyl, propyl, or iso-propyl. In some embodiments, $R^7$ is H or methyl. In some embodiments, $R^7$ is $C_1$-$C_6$alkyl. In some embodiments, $R^7$ is $C_1$-$C_3$alkyl. In some embodiments, $R^7$ is H.

In some embodiments, $R^6$ and $R^7$ are taken together with the carbon atom to which they are attached to form a substituted or unsubstituted $C_3$-$C_6$cycloalkyl ring, or a substituted or unsubstituted $C_3$-$C_6$heterocyclic ring containing 1 or 2 heteroatoms selected from —O—, —$NR^{12}$— and —S—. In some embodiments, $R^6$ and $R^7$ are taken together with the carbon atom to which they are attached to form a substituted or unsubstituted $C_3$-$C_6$cycloalkyl ring. In some embodiments, $R^6$ and $R^7$ are taken together with the carbon atom to which they are attached to form a cyclopropyl ring. In some embodiments, $R^6$ and $R^7$ are taken together with the carbon atom to which they are attached to form a substituted or unsubstituted $C_3$-$C_6$heterocyclic ring containing 1 or 2 heteroatoms selected from —O—, —$NR^{12}$— and —S—.

In some embodiments, $R^8$ is halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —CN, —$NO_2$, —OH, —$OR^{11}$, —$SR^{11}$, —S(═O)$R^{11}$, —S(═O)$_2R^{11}$, —S(═O)$_2$N($R^{12}$)$_2$, —$NR^{12}$S(═O)$_2R^{11}$, —C(═O)$R^{11}$, —OC(═O)$R^{11}$, —$CO_2R^{12}$, —$OCO_2R^{11}$, —N($R^{12}$)$_2$, —C(═O)N($R^{12}$)$_2$, —OC(═O)N($R^{12}$)$_2$, —NHC(═O)$R^{11}$, or —NHC(═O)$OR^{11}$. In some embodiments, $R^8$ is H, halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —OH, —$OR^{11}$, —$SR^{11}$, —S(═O)$R^{11}$, —$S(═O)_2R^{11}$, —C(═O)$R^{11}$, —$CO_2R^{12}$, —$N(R^{12})_2$, or —C(═O)$N(R^{12})_2$. In some embodiments, $R^8$ is halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —OH, —$OR^{11}$, —$SR^{11}$, —S(═O)$R^{11}$, —$S(═O)_2R^{11}$, —C(═O)$R^{11}$, —$CO_2R^{12}$, —$N(R^{12})_2$, or —C(═O)$N(R^{12})_2$. In some embodiments, $R^8$ is H, halogen, $C_1$-$C_6$alkyl, $C_1$-$C_6$fluoroalkyl, $C_1$-$C_6$cycloalkyl, $C_1$-$C_6$hydroxyalkyl, or $C_1$-$C_6$heteroalkyl. In some embodiments, $R^8$ is halogen, $C_1$-$C_6$alkyl, $C_1$-$C_6$fluoroalkyl, $C_1$-$C_6$cycloalkyl, $C_1$-$C_6$hydroxyalkyl, or $C_1$-$C_6$heteroalkyl. In other embodiments, $R^8$ is H, F, Cl, Br, $C_1$-$C_6$alkyl, $C_1$-$C_6$fluoroalkyl, $C_1$-$C_6$cycloalkyl, $C_1$-$C_6$hydroxyalkyl, or $C_1$-$C_6$heteroalkyl. In other embodiments, $R^8$ is F, Cl, Br, $C_1$-$C_6$alkyl, $C_1$-$C_6$fluoroalkyl, $C_1$-$C_6$cycloalkyl, $C_1$-$C_6$hydroxyalkyl, or $C_1$-$C_6$heteroalkyl. In other embodiments, $R^8$ is F, Cl, Br, methyl, ethyl, propyl, isopropyl, butyl, isobutyl, sec-butyl, tertiary butyl, pentyl, neopentyl, hexyl, cyclopropyl, or cyclobutyl. In some embodiments, $R^8$ is methyl, ethyl, propyl, isopropyl, butyl, isobutyl, sec-butyl, tert-butyl, pentyl, neopentyl, hexyl, cyclopropyl, or cyclobutyl. In some embodiments, $R^8$ is methyl, ethyl, propyl, isopropyl, butyl, isobutyl, sec-butyl, or tert-butyl. In some embodiments, $R^8$ is H.

In some embodiments, $R^9$ is halogen, $C_1$-$C_6$alkyl, $C_1$-$C_6$hydroxyalkyl, $C_1$-$C_6$heteroalkyl, —CN, —$NO_2$, —OH, —$OR^{11}$, —$SR^{11}$, —S(═O)$R^{11}$, —$S(═O)_2R^{11}$, —$S(═O)_2N(R^{12})_2$, —$NR^{12}S(═O)_2R^{11}$, —C(═O)$R^{11}$, —OC(═O)$R^{11}$, —$CO_2R^{12}$, —$OCO_2R^{11}$, —$N(R^{12})_2$, —C(═O)$N(R^{12})_2$, —OC(═O)$N(R^{12})_2$, —NHC(═O)$R^{11}$, or —NHC(═O)$OR^{11}$. In other embodiments, $R^9$ is F, Cl, Br, $C_1$-$C_6$alkyl, $C_1$-$C_6$hydroxyalkyl, $C_1$-$C_6$heteroalkyl, —OH, —$OR^{11}$, —$S(═O)_2R^{11}$, —$S(═O)_2N(R^{12})_2$, —$NR^{12}S(═O)_2R^{11}$, —C(═O)$R^{11}$, —$CO_2R^{12}$, —$N(R^{12})_2$, —C(═O)$N(R^{12})_2$, or —NHC(═O)$R^{11}$. In other embodiments, $R^9$ is F, Cl, Br, $C_1$-$C_6$alkyl, $C_1$-$C_6$hydroxyalkyl, $C_1$-$C_6$heteroalkyl, —OH, or —$OR^{11}$. In certain embodiments, $R^9$ is F, Cl, Br, $C_1$-$C_6$hydroxyalkyl, $C_1$-$C_6$heteroalkyl, —OH, or —$OR^{11}$, wherein $R^{11}$ is $C_1$-$C_6$alkyl. In some embodiments, $R^9$ is F, Cl, Br, methyl, ethyl, propyl, isopropyl, butyl, isobutyl, sec-butyl, tert-butyl, pentyl, neopentyl, hexyl, $C_1$-$C_6$hydroxyalkyl, $C_1$-$C_6$heteroalkyl, —OH, methoxy, ethoxy, propoxy, butoxy. In certain embodiments, $R^9$ is OH. In certain embodiments, $R^9$ is H.

In some embodiments, each $R^{10}$ is independently H, halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —OH, —$OR^{11}$, —$SR^{11}$, —S(═O)$R^{11}$, —$S(═O)_2R^{11}$, —C(═O)$R^{11}$, —$CO_2R^{12}$, —$N(R^{12})_2$, or —C(═O)$N(R^{12})_2$. In some embodiments, each $R^{10}$ is independently halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —OH, —$OR^{11}$, —$SR^{11}$, —S(═O)$R^{11}$, —$S(═O)_2R^{11}$, —C(═O)$R^{11}$, —$CO_2R^{12}$, —$N(R^{12})_2$, or —C(═O)$N(R^{12})_2$. In some embodiments, $R^{10}$ is H, F, Cl, Br, $C_1$-$C_6$alkyl, $C_1$-$C_6$fluoroalkyl, $C_1$-$C_6$cycloalkyl, $C_1$-$C_6$hydroxyalkyl, or $C_1$-$C_6$heteroalkyl. In other embodiments, $R^{10}$ is F, Cl, Br, $C_1$-$C_6$alkyl, $C_1$-$C_6$fluoroalkyl, $C_1$-$C_6$cycloalkyl, $C_1$-$C_6$hydroxyalkyl, or $C_1$-$C_6$heteroalkyl. In some embodiments, $R^{10}$ is H, F, Cl, Br, $C_1$-$C_6$alkyl, $C_1$-$C_6$fluoroalkyl, or $C_1$-$C_6$cycloalkyl. In other embodiments, $R^{10}$ is F, Cl, Br, $C_1$-$C_6$alkyl, $C_1$-$C_6$fluoroalkyl, or $C_1$-$C_6$cycloalkyl. In some embodiments, $R^{10}$ is H, F, Cl, Br, methyl, ethyl, propyl, isopropyl, butyl, isobutyl, sec-butyl, tertiary butyl, pentyl, neopentyl, hexyl, cyclopropyl, or cyclobutyl. In other embodiments, $R^{10}$ is F, Cl, Br, methyl, ethyl, propyl, isopropyl, butyl, isobutyl, sec-butyl, tertiary butyl, pentyl, neopentyl, hexyl, cyclopropyl, or cyclobutyl. In other embodiments, $R^{10}$ is methyl, ethyl, propyl, isopropyl, butyl, isobutyl, sec-butyl, or tertiary butyl. In some embodiments, $R^{10}$ is H.

In some embodiments, n is 0. In some embodiments, n is 1. In some embodiments, n is 2. In some embodiments, n is 3. In some embodiments, n is 1, 2 or 3. In some embodiments, n is 2 or 3.

In some embodiments, m is 0. In some embodiments, m is 1. In some embodiments, m is 2. In some embodiments, m is 3. In some embodiments, m is 0 or 1. In some embodiments, m is 1 or 2.

Some embodiments provided herein describe compounds of formula (I), wherein:

each $R^1$ is independently H, halogen, $C_1$-$C_6$alkyl, $C_1$-$C_6$fluoroalkyl, $C_3$-$C_6$cycloalkyl $R^2$ and $R^3$ are taken together with the carbon atom to which they are attached to form —C(═O)—, —C(═$NR^{13}$)—, —C(═N—$OR^{13}$)—, or a heterocyclic ring containing 2 O atoms;

$R^{13}$ is H or $C_1$-$C_6$alkyl;

$R^4$ is H, halogen, $C_1$-$C_6$alkyl, $C_1$-$C_6$fluoroalkyl, or $C_1$-$C_6$deuteroalkyl;

$R^5$ is H, halogen, $C_1$-$C_6$alkyl, $C_1$-$C_6$fluoroalkyl, or $C_1$-$C_6$deuteroalkyl;

$R^6$ is H, halogen, $C_1$-$C_6$alkyl, $C_1$-$C_6$fluoroalkyl, or $C_1$-$C_6$deuteroalkyl; and $R^7$ is H, halogen, $C_1$-$C_6$alkyl, $C_1$-$C_6$fluoroalkyl, or $C_1$-$C_6$deuteroalkyl.

Some embodiments provided herein describe compounds of formula (I), wherein:

each $R^1$ is independently H, halogen, $C_1$-$C_6$alkyl, $C_1$-$C_6$fluoroalkyl, $C_3$-$C_6$cycloalkyl $R^2$ and $R^3$ are taken together with the carbon atom to which they are attached to form —C(═O)—;

$R^4$ is H, halogen, methyl, ethyl, cyclopropyl or cyclobutyl;

$R^5$ is H, halogen, methyl, ethyl, cyclopropyl or cyclobutyl;

$R^6$ is H, halogen, methyl, ethyl, cyclopropyl or cyclobutyl; and $R^7$ is H, halogen, methyl, ethyl, cyclopropyl or cyclobutyl.

Some embodiments provided herein describe compounds of formula (I), wherein:

each $R^1$ is independently H, halogen, $C_1$-$C_6$alkyl, $C_1$-$C_6$fluoroalkyl, $C_3$-$C_6$cycloalkyl $R^2$ and $R^3$ are taken together with the carbon atom to which they are attached to form —C(═O)—;

$R^4$ is H, F, Cl, or methyl;

$R^5$ is H, F, Cl, or methyl;

$R^6$ is H, F, Cl, or methyl; and $R^7$ is H, F, Cl, or methyl.

In one aspect, the compound of Formula (I), or a pharmaceutically acceptable salt, or solvate thereof, has the following structure of Formula (II):

Formula (II)

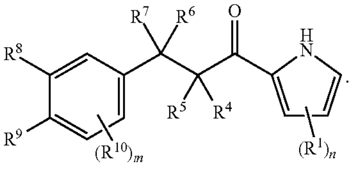

In one aspect, the compound of Formula (I), or a pharmaceutically acceptable salt, or solvate thereof, has the following structure of Formula (III):

Formula (III)

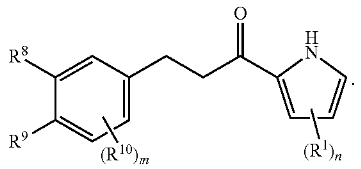

In one aspect, the compound of Formula (I), or a pharmaceutically acceptable salt, or solvate thereof, has the following structure of Formula (IV):

Formula (IV)

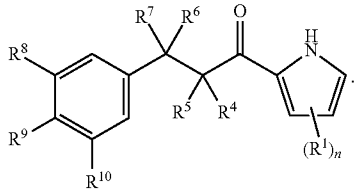

In one aspect, the compound of Formula (I), or a pharmaceutically acceptable salt, or solvate thereof, has the following structure of Formula (V):

Formula (V)

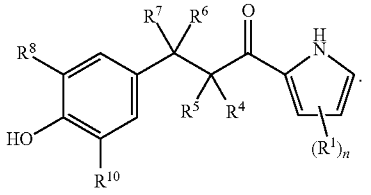

In one aspect, the compound of Formula (I), or a pharmaceutically acceptable salt, or solvate thereof, has the following structure of Formula (VI):

Formula (VI)

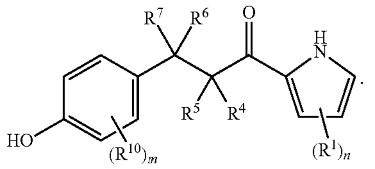

For any and all of the embodiments, substituents are selected from among a subset of the listed alternatives.

Any combination of the groups described above for the various variables is contemplated herein. Throughout the specification, groups and substituents thereof are chosen by one skilled in the field to provide stable moieties and compounds.

Exemplary compounds include the following compounds:

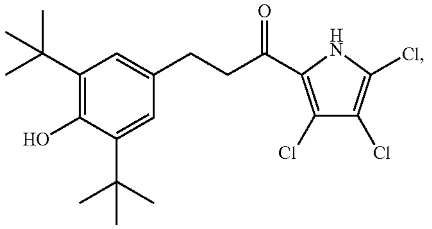

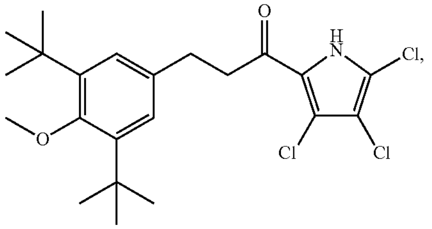

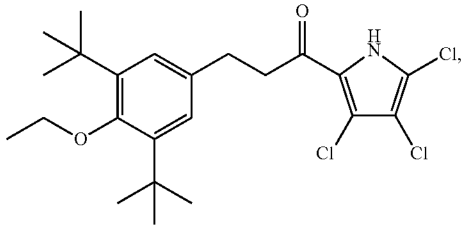

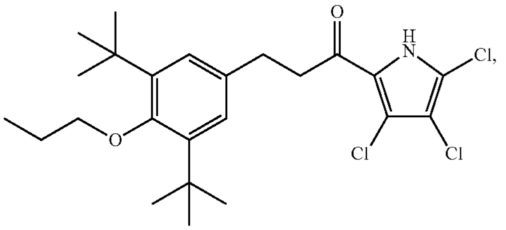

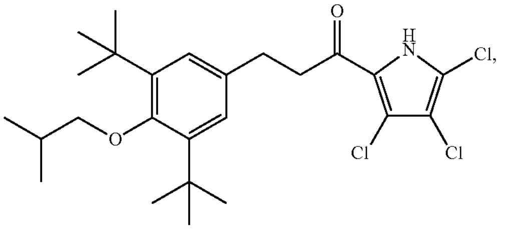

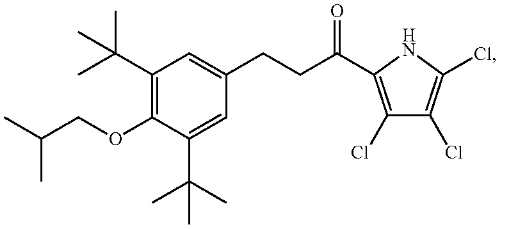

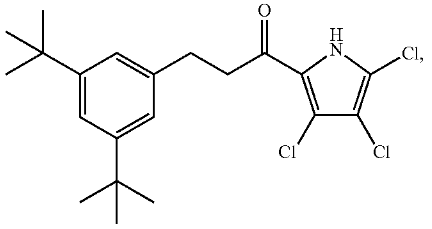

-continued
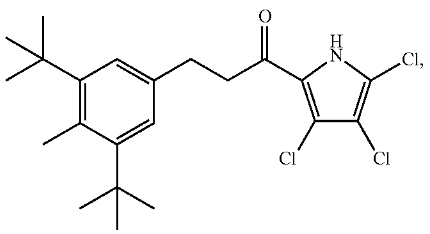
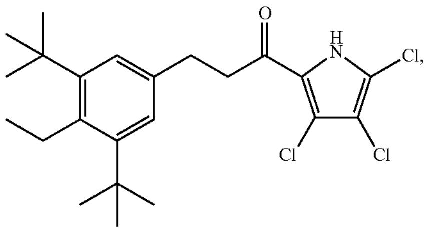
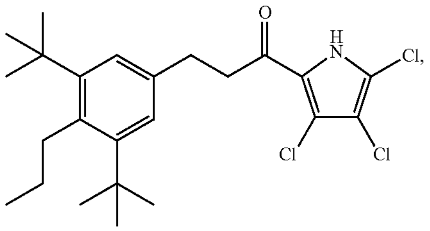
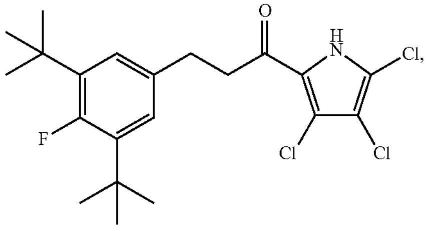
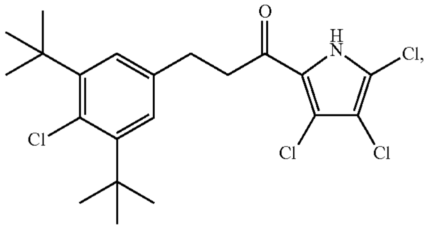
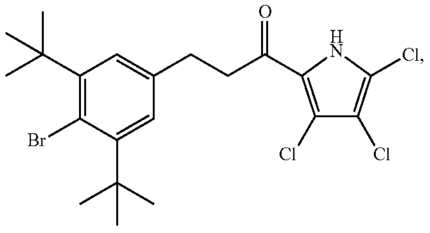
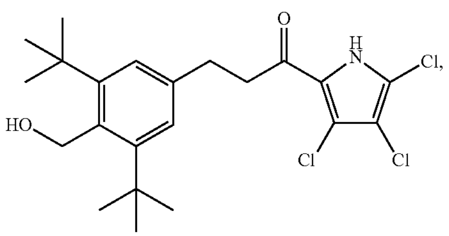
-continued
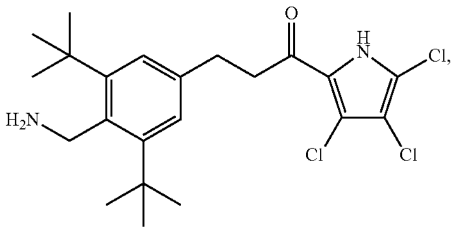
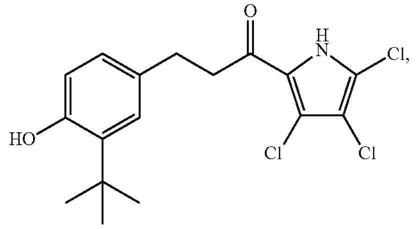
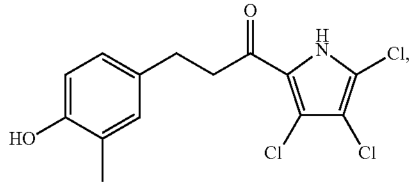
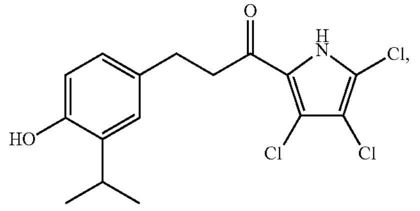
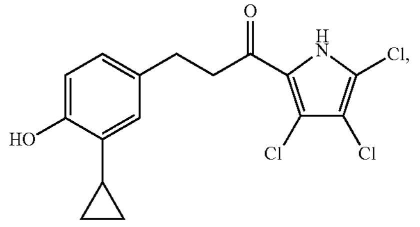
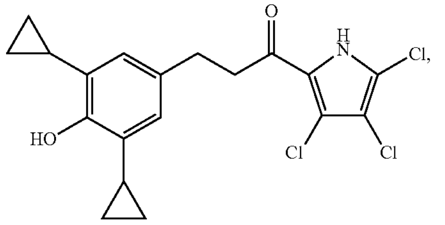
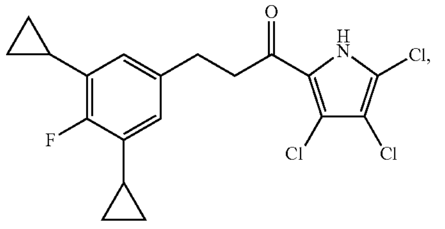
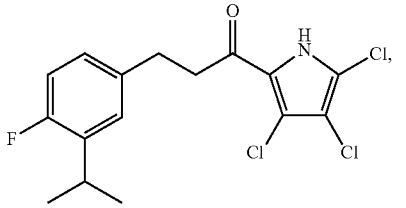

-continued
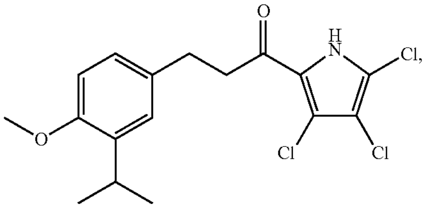
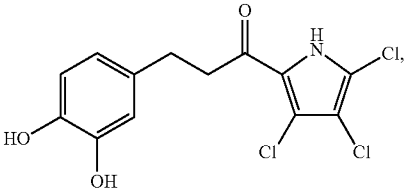
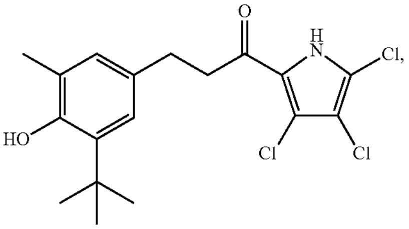
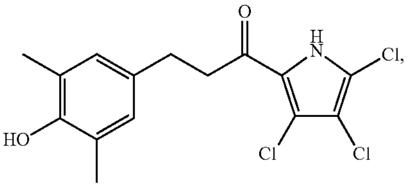
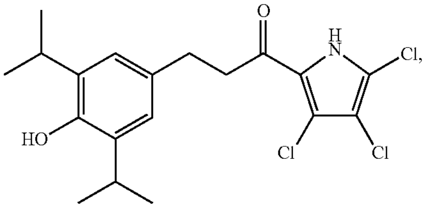
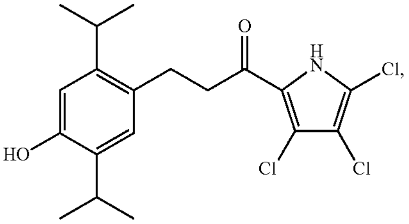
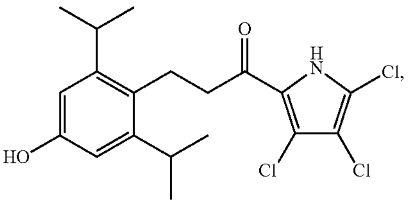
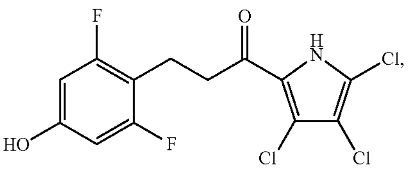
-continued
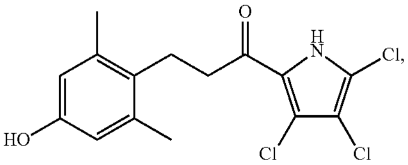
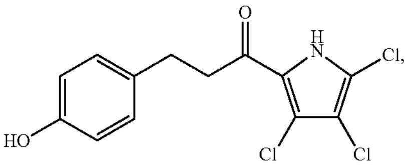
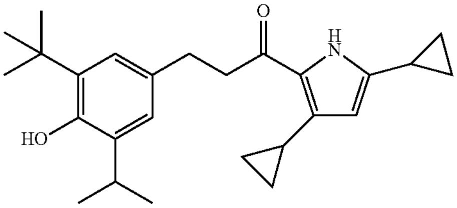
,
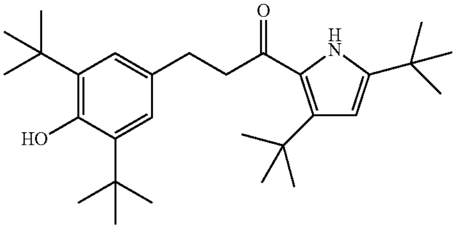
,
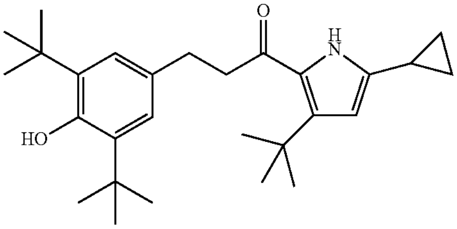
,
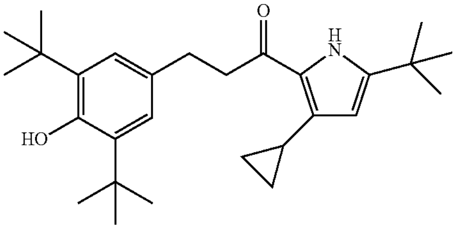
,
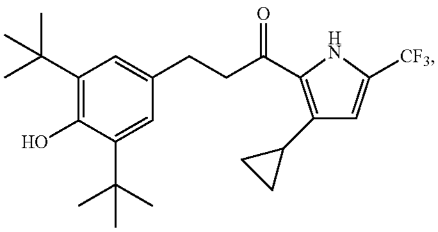
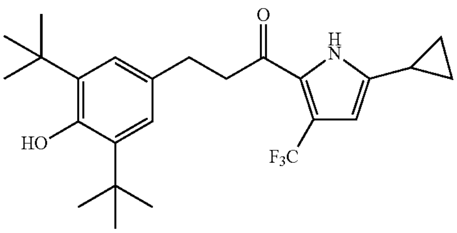
, -continued
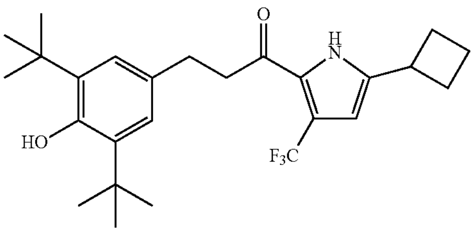
,
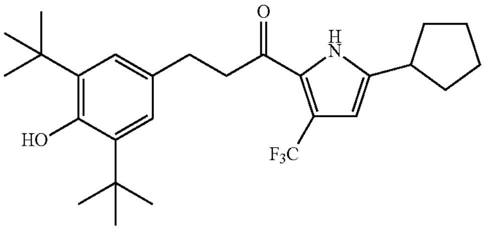
,
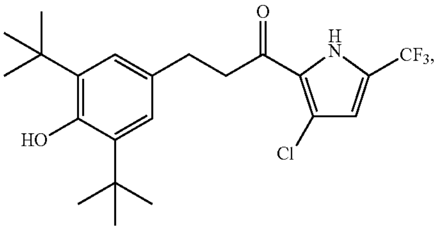
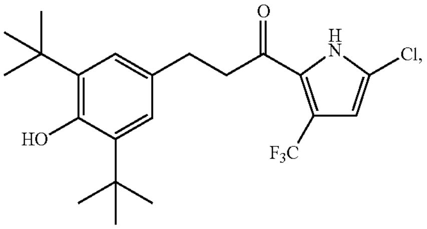
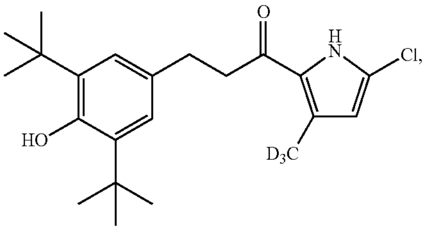
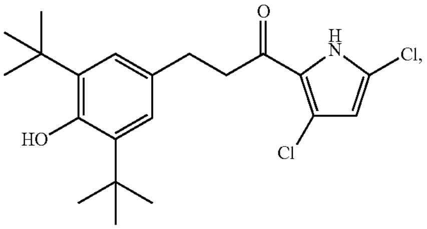
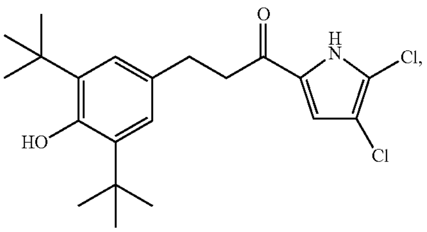
-continued
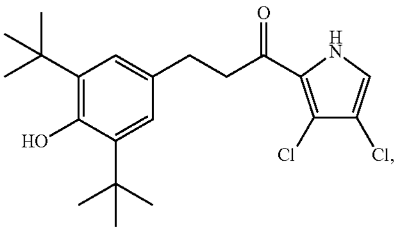
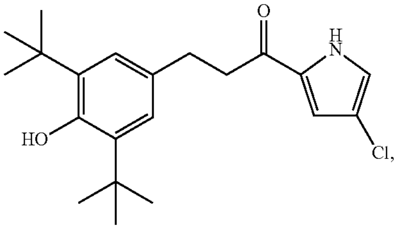
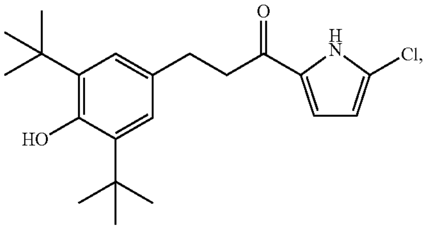
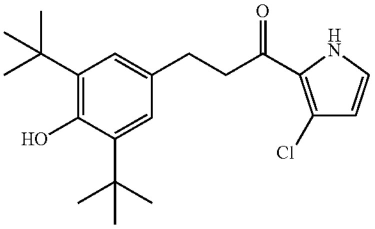
,
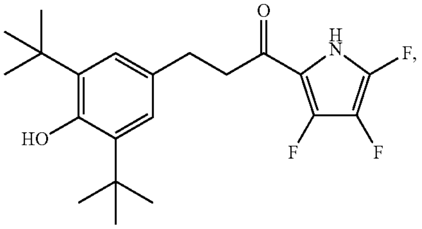
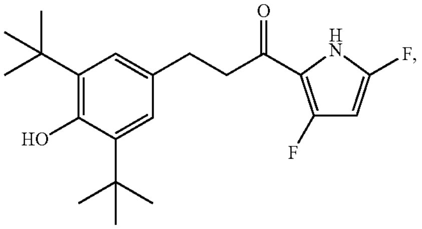
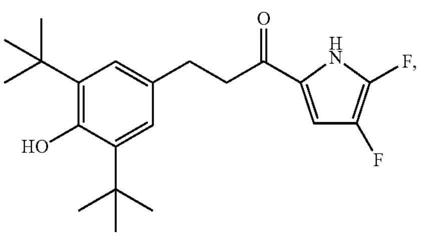

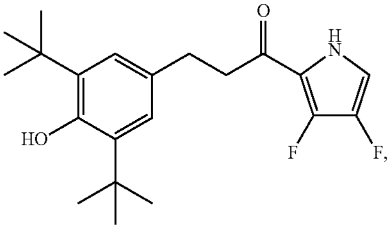
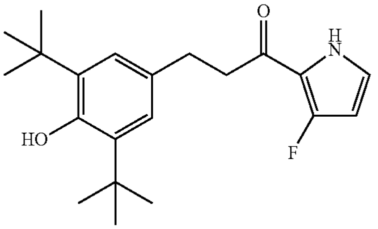
,
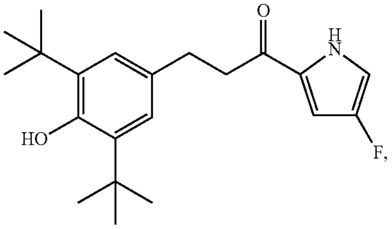
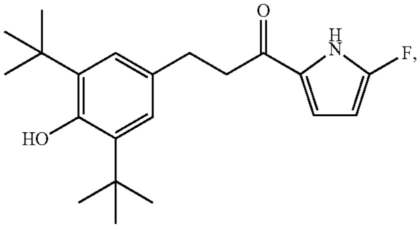
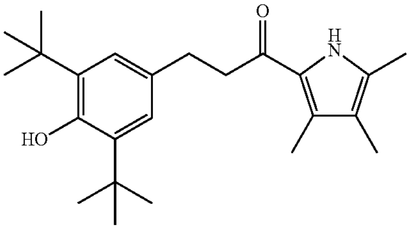
,
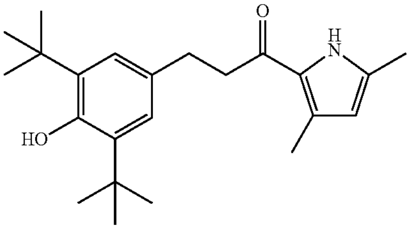
,
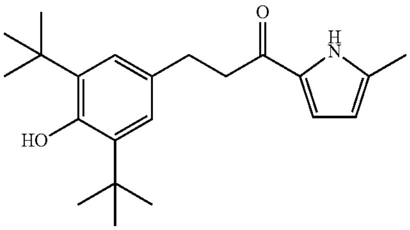
,
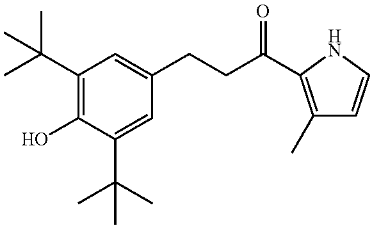
,
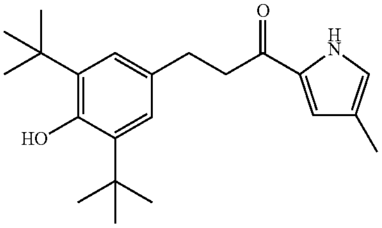
,
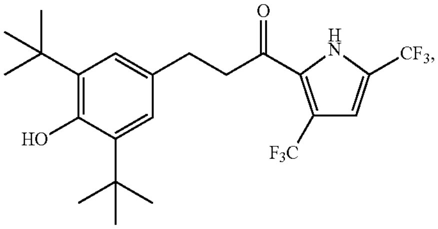
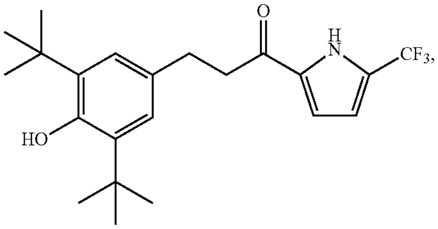
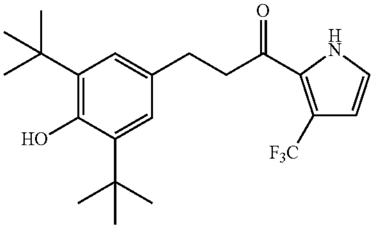
,
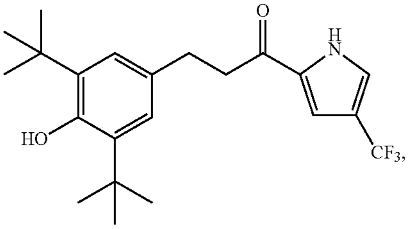
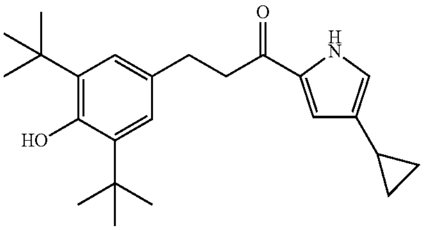
, -continued
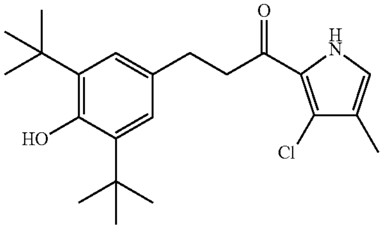
,
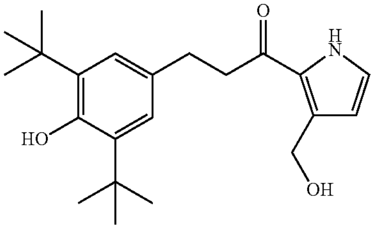
,
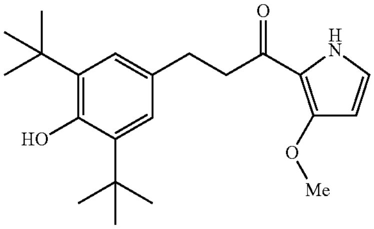
,
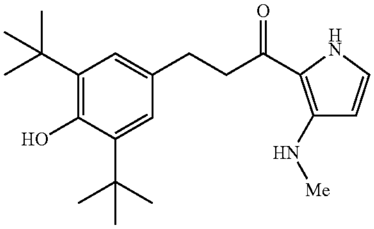
,
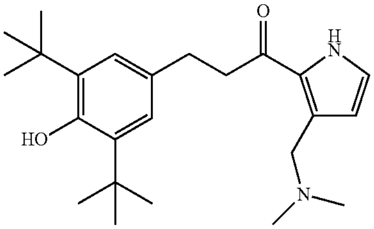
,
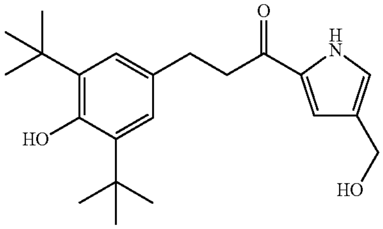
,
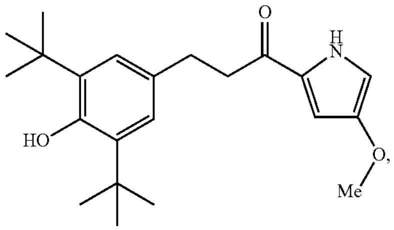
-continued
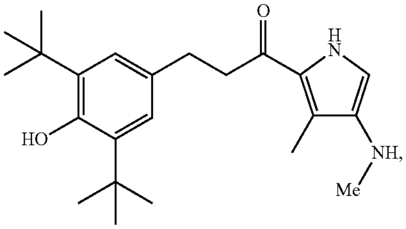
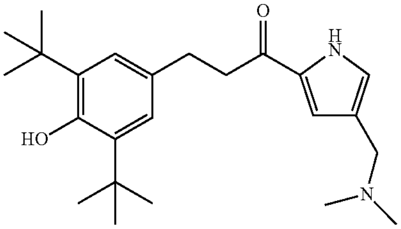
,
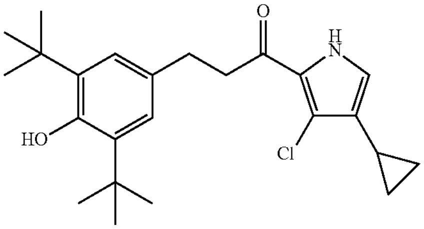
,
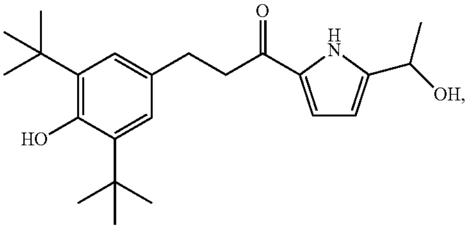
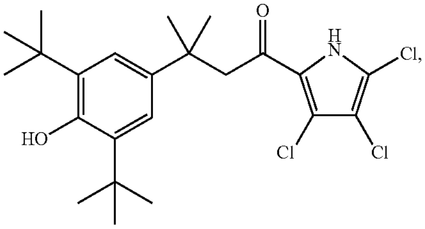
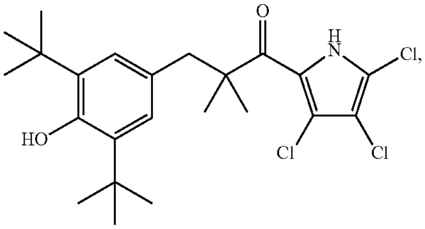
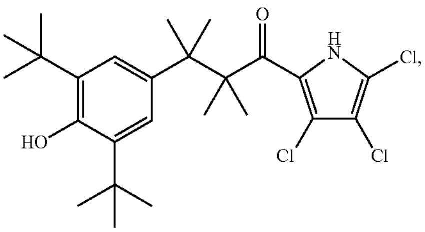

-continued
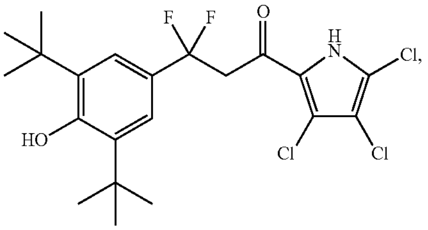
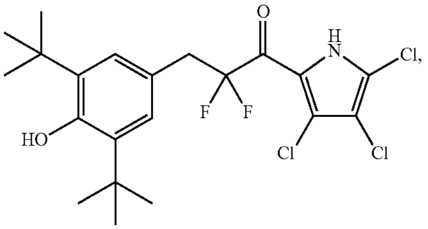
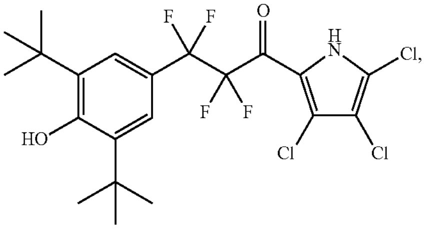
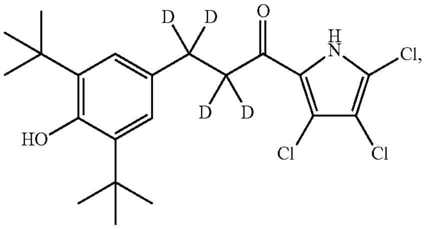
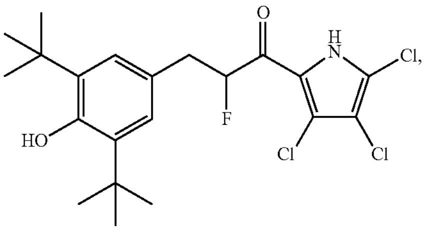
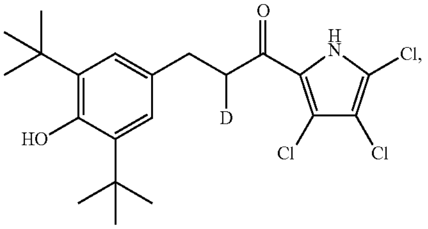
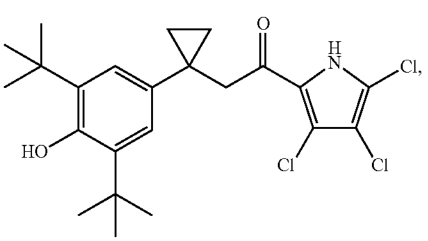
-continued
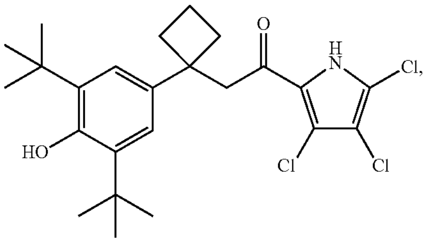
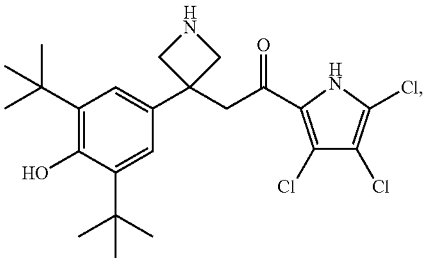
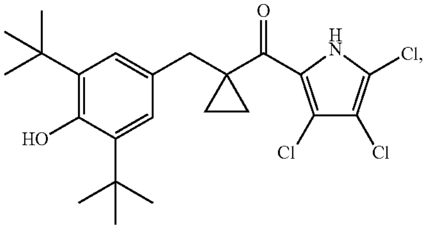
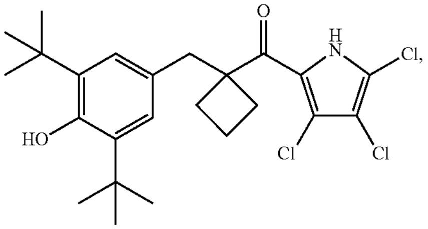
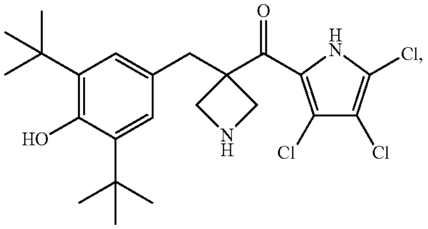
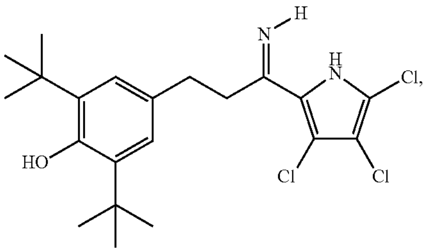
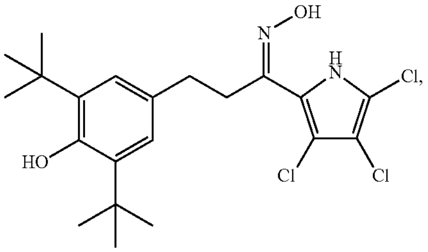

-continued
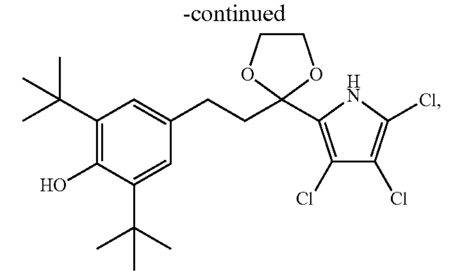
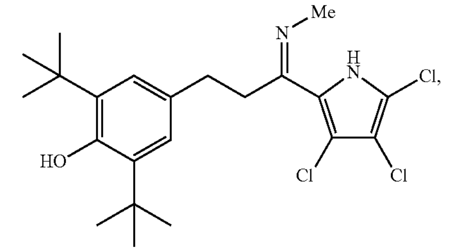
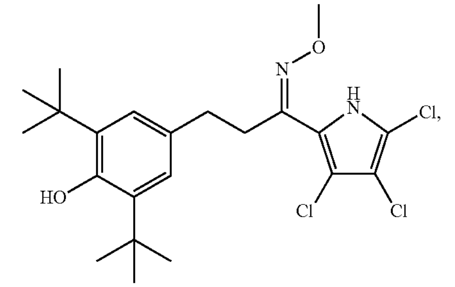
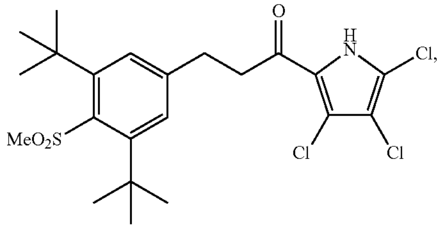
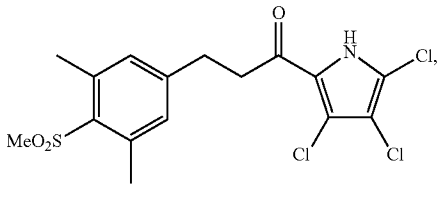
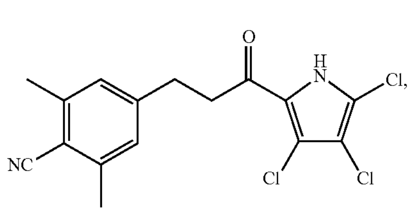
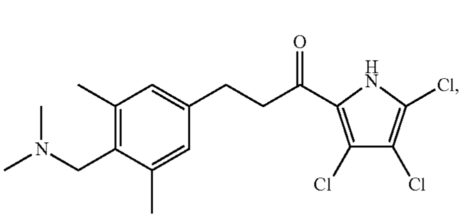
-continued
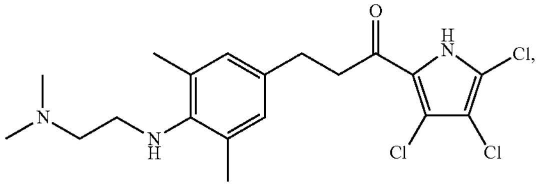
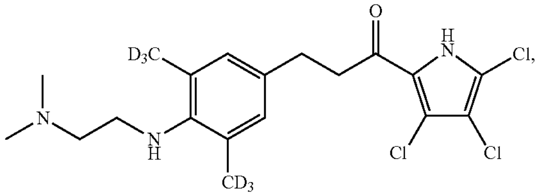
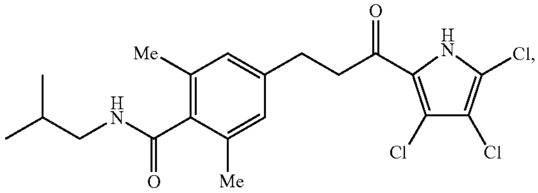
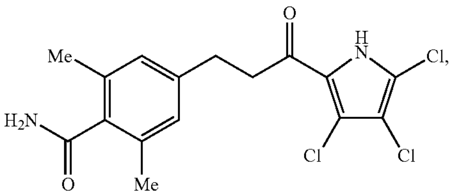
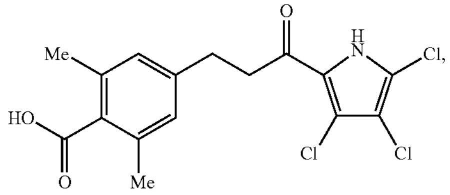
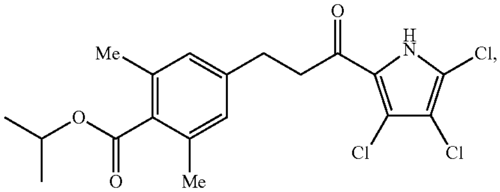
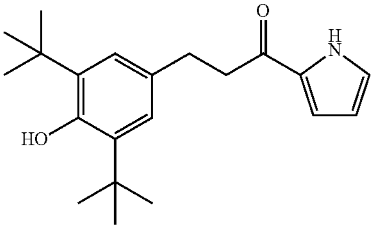
,
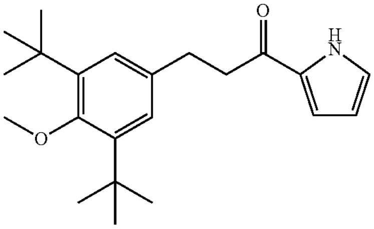
, -continued
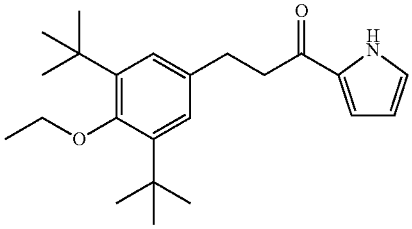
,
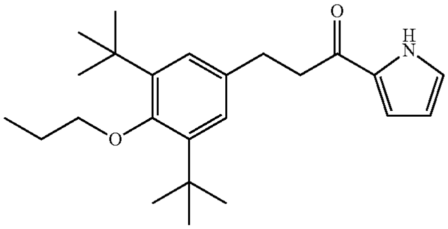
,
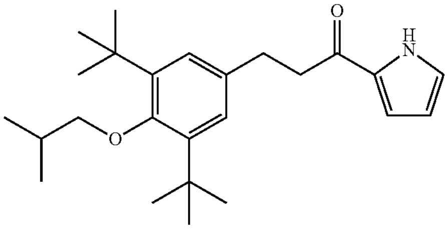
,
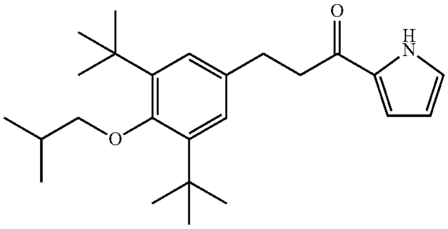
,
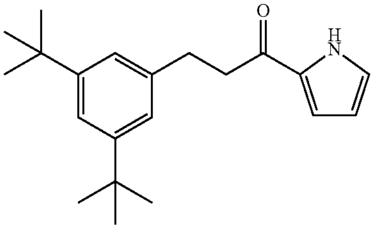
,
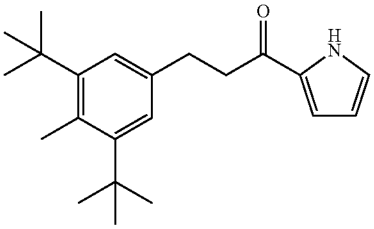
,
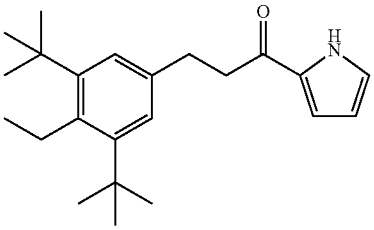
,
-continued
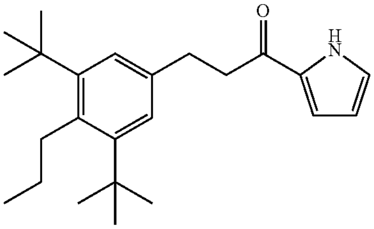
,
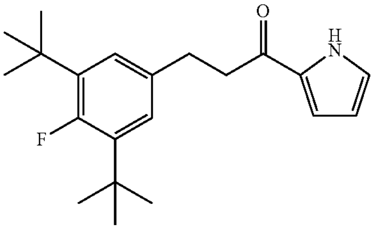
,
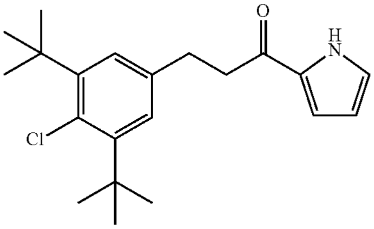
,
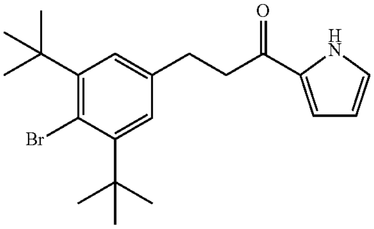
,
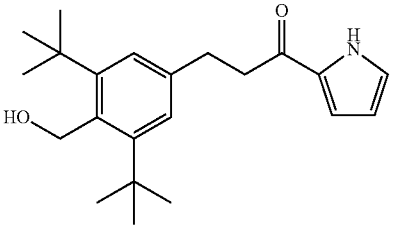
,
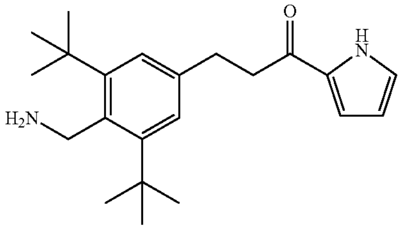
,
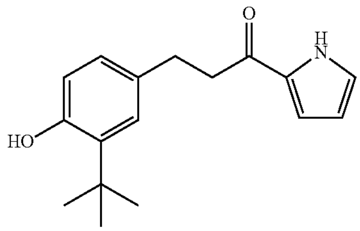
, -continued

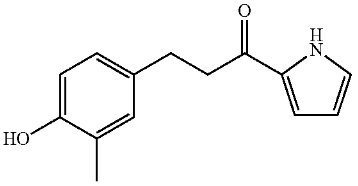
,

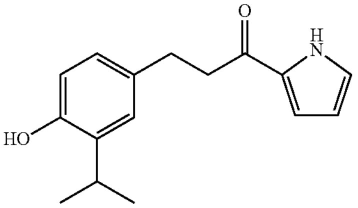
,

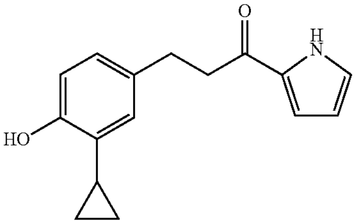
,

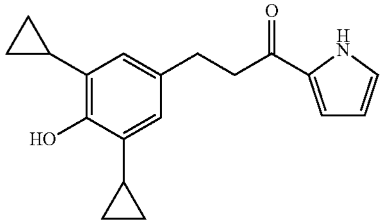
,

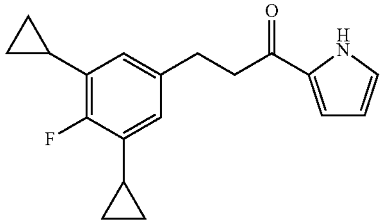
,

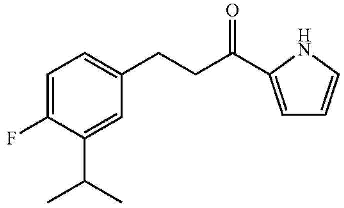
,

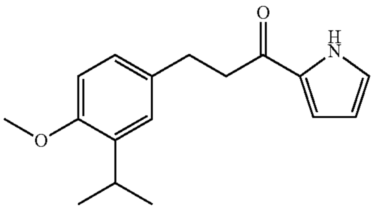
,

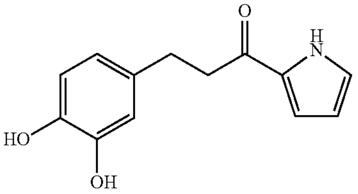
,

-continued

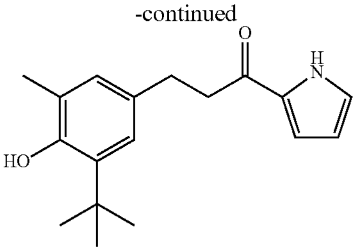
,

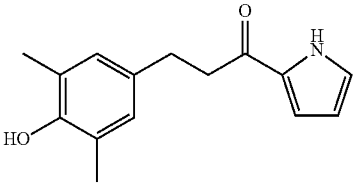
,

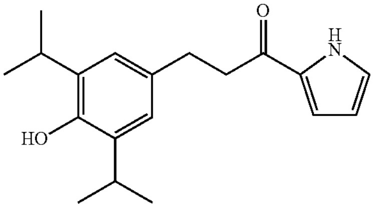
,

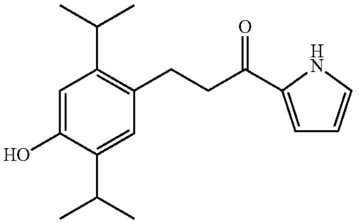
,

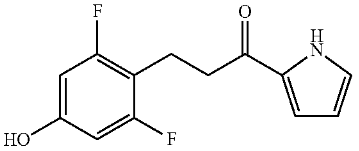
,

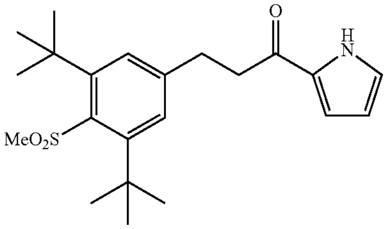
, or

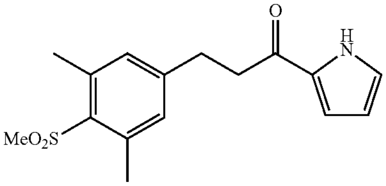
.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound described herein with an acid. In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt. In some embodiments, a compound described herein is prepared as a hydrochloride salt.

In some embodiments, pharmaceutically acceptable salts are obtained by reacting a compound described herein with a base. In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt. In some embodiments, the compounds provided herein are prepared as a sodium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds are prodrugs for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the substituted steroidal derivative compounds described herein is P. H. Stahl & C. G. Wermuth "Handbook of Pharmaceutical Salts", Verlag Helvetica Chimica Acta, Zurich, 2002.

In some embodiments, compounds described herein are prepared by the general synthetic route described below in Scheme 1. Further exemplification is found in the specific examples provided.

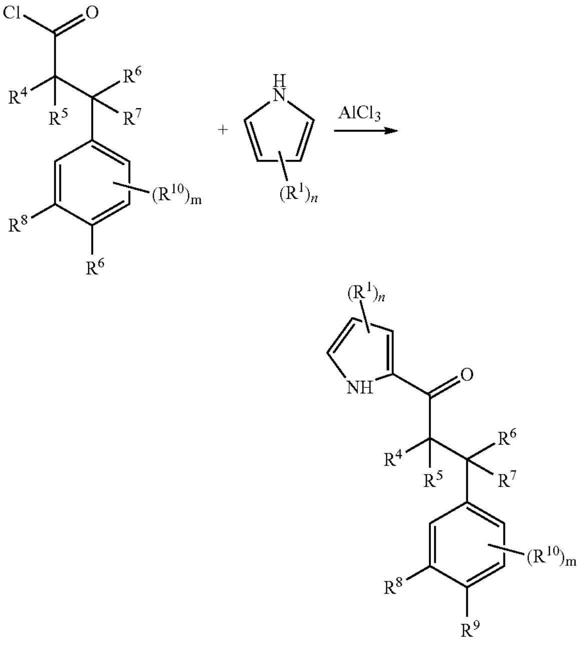

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ . . . $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene.

Typical alkylene groups include, but are not limited to, $—CH_2—$, $—CH(CH_3)—$, $—C(CH_3)_2—$, $—CH_2CH_2—$, $—CH_2CH(CH_3)—$, $—CH_2C(CH_3)_2—$, $—CH_2CH_2CH_2—$, $—CH_2CH_2CH_2CH_2—$, and the like.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula $—C(R)=CR_2$, wherein R refers to the remaining portions of the alkenyl group, which may be the same or different. In some embodiments, R is H or an alkyl. Non-limiting examples of an alkenyl group include $—CH=CH_2$, $—C(CH_3)=CH_2$, $—CH=CHCH_3$, $—C(CH_3)=CHCH_3$, and $—CH_2CH=CH_2$.

The term "alkynyl" refers to a type of alkyl group in which at least one carbon-carbon triple bond is present. In one embodiment, an alkenyl group has the formula $—C≡C≡R$, wherein R refers to the remaining portions of the alkynyl group. In some embodiments, R is H or an alkyl. Non-limiting examples of an alkynyl group include $—C≡CH$, $—C≡CCH_3—C≡CCH_2CH_3$, $—CH_2C≡CH$.

An "alkoxy" group refers to a (alkyl)O— group, where alkyl is as defined herein.

The term "alkylamine" refers to the $—N(alkyl)_xH_y$ group, where x is 0 and y is 2, or where x is 1 and y is 1, or where x is 2 and y is 0.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1]pentyl. In some embodiments, a cycloalkyl is a $C_3$-$C_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoralkyl is a $C_1$-$C_6$fluoroalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, $—NH_2$, —NH(alkyl), $—N(alkyl)_2$, —OH, $—CO_2H$, $—CO_2alkyl$, $—C(=O)NH_2$, —C(=O)NH(alkyl), $—C(=O)N(alkyl)_2$, $—S(=O)_2NH_2$, $—S(=O)_2NH(alkyl)$, $—S(=O)_2N(alkyl)_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, $—NH_2$, $—NH(CH_3)$, $—N(CH_3)_2$, —OH, $—CO_2H$, $—CO_2(C_1$-$C_4alkyl)$, $—C(=O)NH_2$, $—C(=O)NH(C_1$-$C_4alkyl)$, $—C(=O)N(C_1$-$C_4alkyl)_2$, $—S(=O)_2NH_2$, $—S(=O)_2NH(C_1$-$C_4alkyl)$, $—S(=O)_2N(C_1$-$C_4alkyl)_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, $—SC_1$-$C_4$alkyl, $—S(=O)C_1$-$C_4$alkyl, and $—S(=O)_2C_1$-$C_4$alkyl. In some embodiments, optional substituents are independently selected from halogen, —CN, $—NH_2$, —OH, $—NH(CH_3)$, $—N(CH_3)_2$, $—CH_3$, $—CH_2CH_3$, $—CF_3$, $—OCH_3$, and $—OCF_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader. In some embodiments, a modulator is an inhibitor.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from inhibition or reduction of CRAC channel activity. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents. In certain embodiments, the pharmaceutical composition further comprises one or more anti-cancer agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder or condition being treated, thereby providing a greater overall benefit than administration of either therapeutic agent alone. In some embodiments, the second therapeutic agent is an anti-inflammatory agent, anti-cancer agent, immunosuppressive agent, steroid, non-steroidal anti-inflammatory agent, antihistamine, analgesic, hormone blocking therapy, radiation therapy, monoclonal antibodies, or combinations thereof. In some embodiments, the second therapeutic agent is an anti-inflammatory agent, anti-cancer agent, immunosuppressive agent, steroid, non-steroidal anti-inflammatory agent, antihistamine, or analgesic. In some embodiments, the second therapeutic agent is an anti-cancer agent.

In any case, regardless of the disease, disorder or condition being treated, the overall benefit experienced by the patient is simply additive of the two therapeutic agents or the patient experiences a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, a compound described herein, or a pharmaceutically acceptable salt thereof, is administered in combination with anti-inflammatory agent, anti-cancer agent, immunosuppressive agent, steroid, non-steroidal anti-inflammatory agent, antihistamine, analgesic, hormone blocking therapy, radiation therapy, monoclonal antibodies, or combinations thereof.

EXAMPLES

The following examples are provided for illustrative purposes only and not to limit the scope of the claims provided herein.

Example 1: Synthesis of 3-(3,5-di-tert-butyl-4-hydroxyphenyl)-1-(1H-pyrrol-2-yl)propan-1-one (Compound 1)

Compound 1 was prepared in one step by standard Friedel-Crafts acylation of pyrrole. (See Scheme 1) Mass spectra was recorded on a mass spectrometer using electrospray ionization. Compound 1: $ES^+$ m/z 328.2 $[M+H]^+$, calcd. for $C_{21}H_{29}NO_2$ Exact mass: 327.0.

Example 2: Synthesis of 3-(3,5-di-tert-butyl-4-hydroxyphenyl)-1-(3,4,5-trichloro-1H-pyrrol-2-yl)propan-1-one (Compound 2)

Compound 2 was prepared from Compound 1 by chlorination with molecular chlorine followed by chromatographic purification. Mass spectra was recorded on a mass spectrometer using electrospray ionization. Compound 2: $ES^+$ m/z 430.3 $[M+H]^+$, calcd. for $C_{21}H_{29}Cl_3NO_2$ Exact mass: 429.0.

Example 3: Parenteral Pharmaceutical Composition

To prepare a parenteral pharmaceutical composition suitable for administration by injection (subcutaneous, intravenous), 1-100 mg of a water-soluble salt of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example 4: Oral Solution

To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example 5: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example 6: Oral Capsule

To prepare a pharmaceutical composition for oral delivery, 10-500 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound described herein, or a pharmaceutically acceptable salt thereof, is placed into Size 4 capsule, or size 1 capsule (hypromellose or hard gelatin) and the capsule is closed.

Example 7a: $Ca^{2+}$ Signaling Assay

Compounds of Formula (I) are screened for inhibition of $Ca^{2+}$ signaling by treating human Jurkat T cells with the calcium indicator dye, Fluo-4, to allow for detection of $Ca^{2+}$ influx. Jurkat cells are then cultured with compounds of Formula (I) and activated with Phytohemagglutinin PHA-P to induce $Ca^{2+}$ influx. Immediately after activation, fluorescence is determined on a flow cytometer.

Example 7b: $Ca^{2+}$ Signaling Assay

Figure 2:
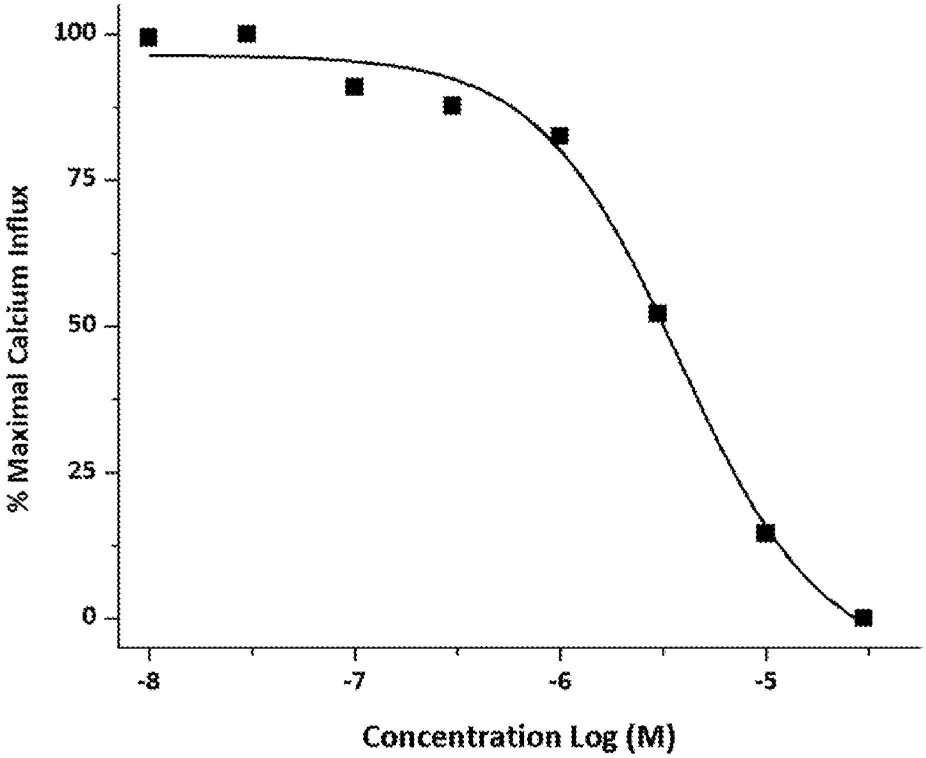
FIG. 2 depicts Compound 2 as a modulator of store-operated $Ca^{2+}$ (SOC) channels.

Compound 2 was screened for inhibition of $Ca^{2+}$ signaling by examining the intracellular $Ca^{2+}$ response in the presence of Compound 2 (FIG. 2). First, the human Jurkat T cells, an immortalized line of human acute T cell lymphoblastic leukemia, were loaded with the 2 μM of the $Ca^{2+}$ indicator dye, Fluo-4, to allow for detection of $Ca^{2+}$ influx. Jurkat cells were then cultured with Compound 2 and activated with Phytohemagglutinin PHA-P to induce $Ca^{2+}$ influx. Immediately after activation, $Ca^{2+}$ influx was determined by measuring Jurkat fluorescence using a flow cytometer. Maximal $Ca^{2+}$ influx occurred with a 2.9 fold increase in mean Fluo-4 fluorescence intensity compared to an unstimulated control. Maximal inhibition of $Ca^{2+}$ influx occurred with a 0.35 fold increase compared to an unstimulated control. Compound 2 potently inhibited $Ca^{2+}$ influx with an $IC_{50}$ of 3.78 μM.

Example 7c: $Ca^{2+}$ Signaling Assay

Figure 8:
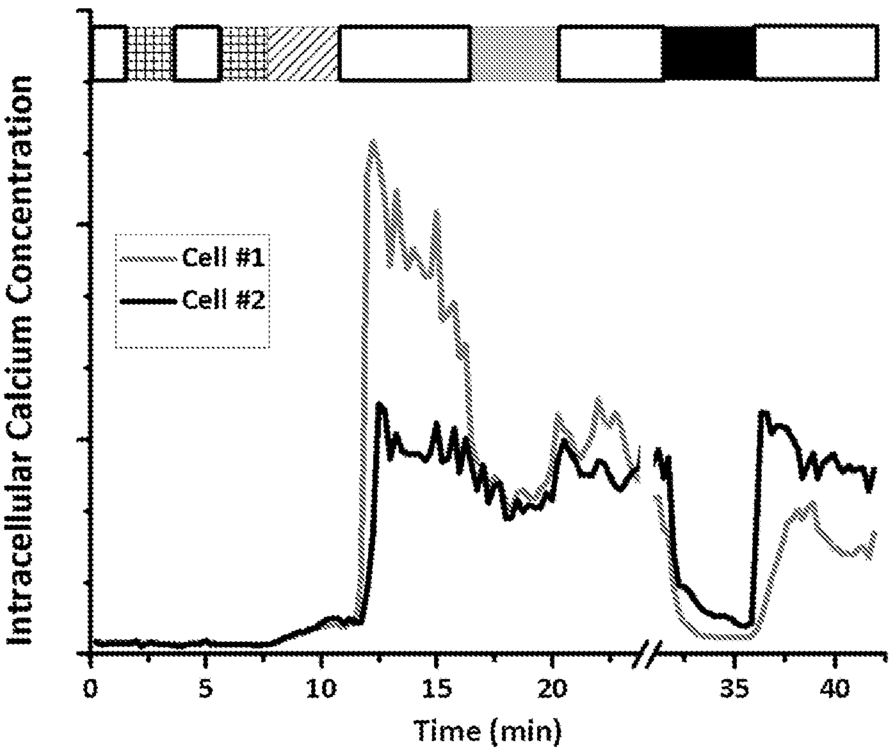
FIG. 8 depicts Compound 1 as a modulator of store-operated $Ca^{2+}$ (SOC) channels. The white rectangle represents a 2 mM external $Ca^{2+}$ concentration solution, the hashed rectangle represents a 0 mM external Ca2+ concentration solution, the slashed rectangle represents a 0 mM external $Ca^{2+}$ concentration solution with 2 μM thapsigargin, the grey rectangle represents 10 μM Compound 1 in a 2 mM external $Ca^{2+}$ concentration solution, and the black rectangle represents 50 M 2-aminoethoxydiphenyl borate in a 2 mM external $Ca^{2+}$ concentration solution. Cell #1 and Cell #2 represent two separate human embryonic kidney 293 cells successfully transfected with recombinant human Orai1 and recombinant human STIM1.

Compound 1 was screened for inhibition of $Ca^{2+}$ signaling by examining the intracellular $Ca^{2+}$ response in the presence of Compound 1 (FIG. 8). First, human embryonic kidney 293 cells were transfected by lipofectamine with recombinant human Orai1 and recombinant human STIM1. Recombinant human Orai1 was genetically tagged with enhanced green fluorescent protein to label successfully transfected cells. Cells were plated on coverslips and loaded with 2 μM of the $Ca^{2+}$ indicator dye, Fura-2, to allow for detection of intracellular $Ca^{2+}$ concentration. Cellular fluorescence was determined by alternating fluorescent excitation at 340 and 380 nanometers. Single cell fluorescence was measured during solution exchanges, indicating that Compound 1 modulates store-operated $Ca^{2+}$ (SOC) channels in CRAC channel transfected human embryonic cells.

Example 8a: $Ca^{2+}$ Signaling Assay

Compounds of Formula (I) are screened for inhibition of $Ca^{2+}$ signaling by treating human Jurkat T cells with the calcium indicator dye, Fluo-4, to allow for detection of $Ca^{2+}$ influx. Jurkat cells are then cultured with compounds of Formula (I) and activated with thapsigargin to induce $Ca^{2+}$ influx. Immediately after activation, fluorescence is determined on a flow cytometer.

Example 8b: Cell Proliferation Assay

Figure 3:
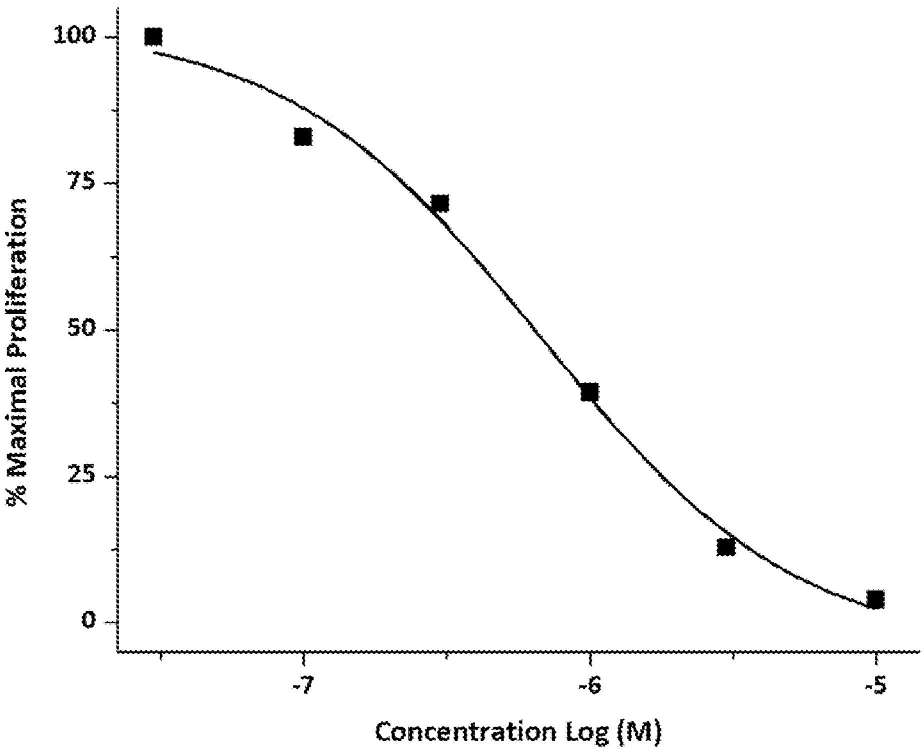
FIG. 3 depicts Compound 2 as a modulator of primary human T cell proliferation.

Compound 2 was screened for inhibition of primary human T cell proliferation by quantifying cellular divisions in the presence of Compound 2 (FIG. 3). First, a 96-well plate was coated with 4 μg/mL anti-CD3 antibody (clone: OKT3) in phosphate buffered saline overnight at 4 degrees Celsius. Primary human T cells were then isolated from the peripheral blood of a healthy, consenting donor using an antibody-based human T cell enrichment protocol. Human T cells were then stained with 1.75 μM of carboxyfluorescein succinimidyl ester, to allow for detection of cellular proliferation. Human T cells were then cultured with Compound 2 and activated with immobilized anti-CD3 and 1 μg/mL soluble anti-CD28 (clone: CD28.2) antibodies and 0.2 ng/mL recombinant human IL-2 to induce cellular proliferation through the NFAT and NF-κB transcription factor pathways. Proliferation was assayed through flow cytometric analysis of carboxyfluorescein succinimidyl ester dilution after 72 hours in standard culture conditions. Maximal proliferation occurred with a 3.9 fold increase in activation index compared to an unstimulated control. Maximal inhibition of proliferation occurred with a 0.91 fold increase compared to an unstimulated control. Compound 2 potently inhibited primary human T cell proliferation with an $IC_{50}$ of 671 nM.

Example 9a: Cell Proliferation Assay

Compounds of Formula (I) are screened for inhibition of leukemic cancer cell proliferation by treating both human Jurkat T cells and human Ramos B cells with the cell-tracker dye carboxyfluorescein succinimidyl ester CFSE to allow for detection of cellular proliferation. Cancer cells are then cultured with compounds of Formula (I) for five days. After the culture period, fluorescence is determined on a flow cytometer.

Example 9b: Cell Proliferation Assay

Figure 4:
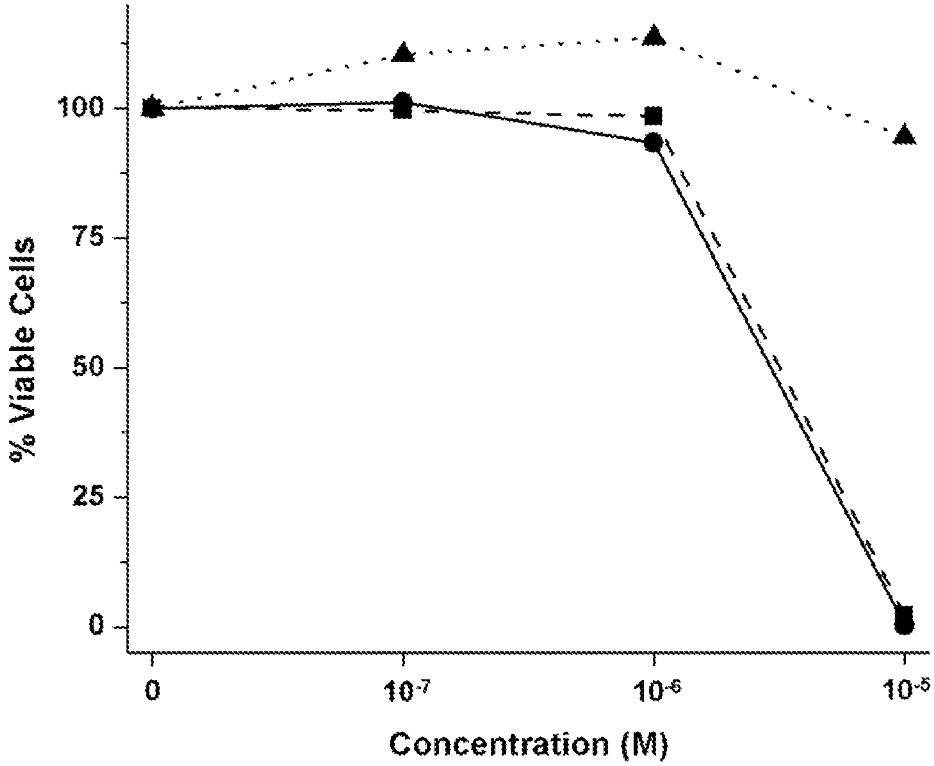
FIG. 4 depicts Compound 2 as a modulator of cancer cell viability.

Compound 2 was screened for inhibition of cancer cell survival by quantifying cellular death in the presence of Compound 2 (FIG. 4). Human Jurkat T cells (■), an immortalized line of human acute T cell lymphoblastic leukemia; Ramos B cells (•), an immortalized line of human Burkitt's lymphoma; and primary human T cells (▲) isolated from the peripheral blood of a healthy, consenting donor were cultured in the presence Compound 2 to test for cellular viability and cell death. Cells were cultured in standard culture conditions, and primary human T cells were also activated with 4 μg/mL immobilized anti-CD3 (clone: OKT3) and 1 μg/mL soluble anti-CD28 (clone: CD28.2) antibodies and 0.2 ng/mL recombinant human IL-2. Cell viability was assayed through flow cytometric analysis of cellular light scatter following 72 hours for primary human or 120 hours for Jurkat and Ramos in standard culture conditions. Viable cell percentage was analyzed as the percent decrease of viable cells compared to a control well with no Compound 2 using a standard flow cytometry lymphocyte analysis gate of forward and side scatter. The viability of Jurkat and Ramos cells decreased in the presence of Compound 2, and the viability of primary human T cells from a healthy donor did not decrease in the presence of Compound 2.

Example 10: $Ca^{2+}$ Signaling Assay in Microglia

Figure 5:
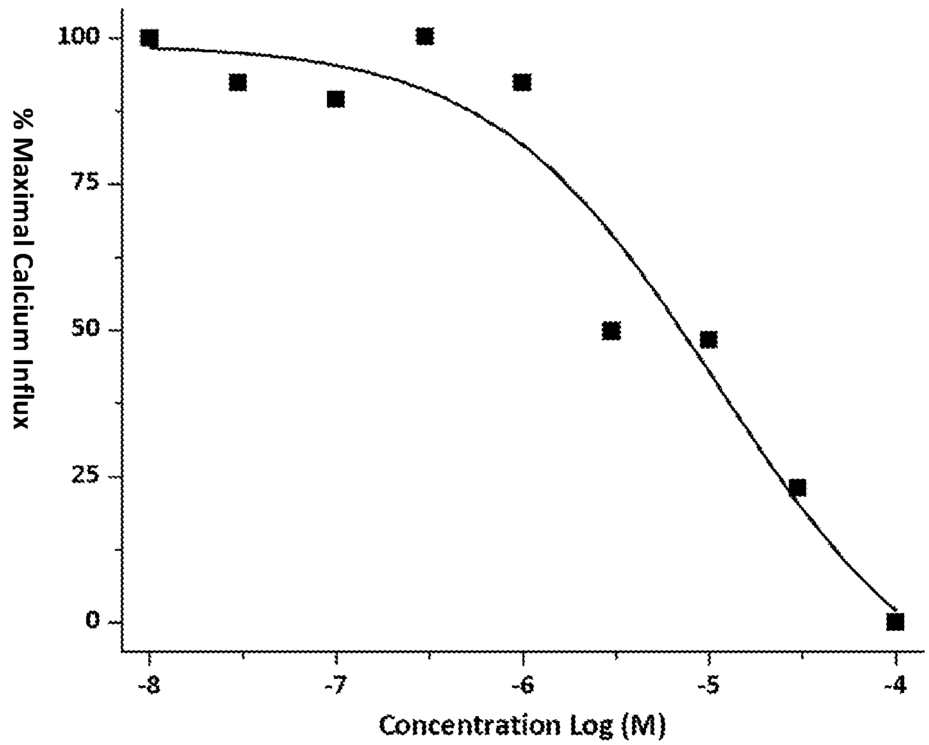
FIG. 5 depicts Compound 2 as a modulator of store-operated $Ca^{2+}$ (SOC) channels in microglia cells.

Compound 2 was screened for inhibition of $Ca^{2+}$ signaling by examining the intracellular $Ca^{2+}$ response in the presence of Compound 2 (FIG. 5). First, the murine cerebellum CRL-2540 cells, an immortalized line of mouse microglia, were loaded with the 2 μM of the $Ca^{2+}$ indicator dye, Fluo-4, to allow for detection of $Ca^{2+}$ influx. CRL-2540 cells were then cultured with Compound 2 and activated with 2 μM thapsigargin to induce $Ca^{2+}$ influx. Immediately after activation, $Ca^{2+}$ influx was determined by measuring CRL-2540 fluorescence using a flow cytometer. Maximal $Ca^{2+}$ influx occurred with a 0.52 fold increase in mean Fluo-4 fluorescence intensity compared to an unstimulated control. Maximal inhibition of $Ca^{2+}$ influx occurred with a 0.19 fold increase compared to an unstimulated control. Compound 2 potently inhibited $Ca^{2+}$ influx with an $IC_{50}$ of 10.9 μM.

Example 11: In Vivo Pharmacokinetics

Figure 6:
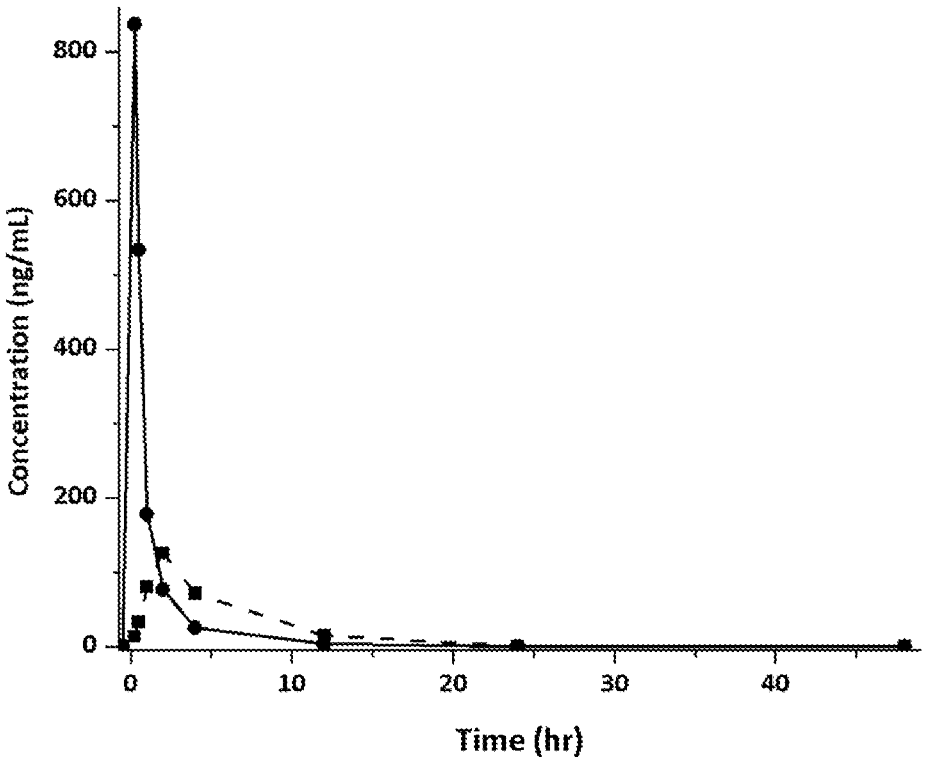
FIG. 6 depicts in vivo pharmacokinetics of Compound 1.

Compound 1 was administered p.o. (■) or i.v. (•) to a nine week old male Sprague Dawley rat (FIG. 6). For survival blood collection, 250-350 μL blood samples were collected via jugular vein (JUGVEIN) cannula at proposed time points per study protocol and recorded. Blood was collected pre-dose and at 15 & 30 min, 1, 2, 4, 12, 24 & 48 hr after Compound 1 administration. Blood was collected into lithium heparin tubes for plasma collection. Calibration standards and study samples were processed for LC/MS/MS analysis by precipitating 40 μL of each sample with two volumes of ice cold Internal Standard Solution (acetonitrile containing 50 ng/mL of dextromethorphan, 5 ng/mL diphenhydramine and 125 ng/mL diclofenac). The precipitated samples were centrifuged at 6100 g for 30 minutes. Following centrifugation, an aliquot of each supernatant was transferred to an autosampler plate and diluted with an equal volume of 0.2% formic acid in water. Processed study samples were analyzed using LC/MS/MS. For the i.v. route, the dose was 10000 μg/kg, Cmax 0.837 μg/mL, Tmax 0.250 hr, CL 14174 mL/hr/kg, VSS 26904 mL/kg, MRTinf 1.90 hr, AUClast 0.694 hr*μg/mL, AUC0-inf 0.706 hr*μg/mL, and Terminal t½ 2.64 h. For the p.o. route, the dose was 10000 μg/kg, Cmax 0.126 μg/mL, Tmax 2 hr, AUClast 0.679 hr*μg/mL, AUC0-inf 0.747 hr*μg/mL, T½ 3.27 hr, and bioavailability 106%. Animal body weight and clinical observations appeared normal throughout the study.

Example 12: MDCK-MDR1 Permeability Assay

Figure 7:
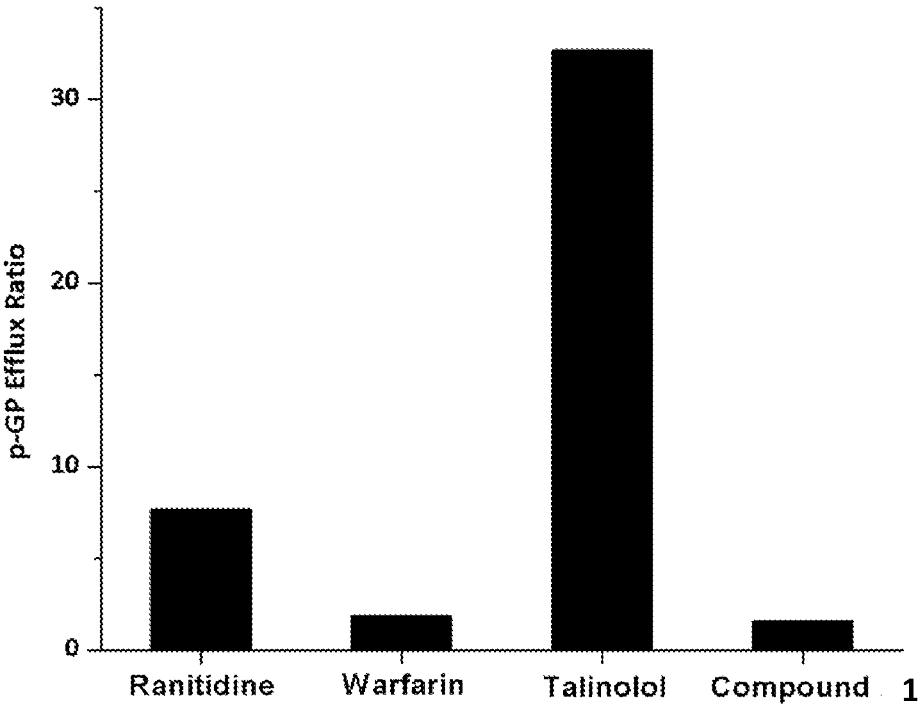
FIG. 7 depicts MDCK-MDR1 permeability of Compound 1.

Compound 1 was evaluated for permeability across polarized Madin-Darby canine kidney-multidrug resistance protein 1 (MDCK-MDR1) epithelial monolayers. MDCK-MDR1 cells grown in tissue culture flasks were trypsinized, suspended in medium, and the suspensions were applied to wells of a Millipore 96 well Caco-2 plate (FIG. 7). The cells were allowed to grow and differentiate for five days and confluence was confirmed. For Apical to Basolateral (A→B) permeability, Compound 1 was added to the apical (A) side and amount of permeation is determined on the basolateral (B) side; for Basolateral to Apical (B→A) permeability, the Compound 1 was added to the B side and the amount of permeation was determined on the A side and analyzed by LC/MS/MS. Ranitidine is a "low permeability" control; warfarin "high permeability" control; and talinolol "efflux control." Compound 1 had a mean A→B $P_{app}{}^{a}$ of $1.0*10^{-6}$ cm $s^{-1}$, mean B→A $P_{app}{}^{a}$ of $1.6*10^{-6}$ cm $s^{-1}$, and an efflux ratio of 1.6.

Example 13: Human Acute Monocytic Leukemia THP1 Cell Assay

Figure 9:
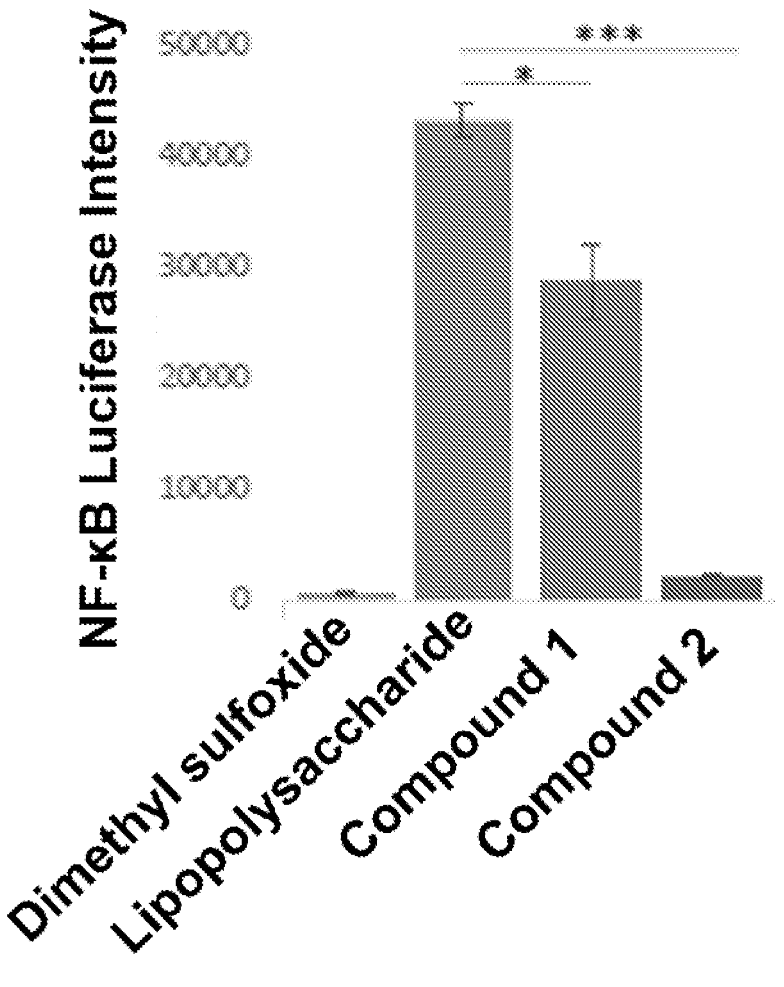
FIG. 9 depicts levels of NF-κB Lucia in THP1 cells activated by lipopolysaccharide in the presence of dimethyl sulfoxide, 30 μM Compound 1 or 30 μM Compound 2.

Compounds 1 and 2 were screened for inhibition of inflammatory transcription using human acute monocytic leukemia THP1 cells stably transfected with a nuclear factor kappa-light-chain-enhancer of activated B cells (NF-κB)-luciferase reporter gene. THP1 cells were activated by lipopolysaccharide in the presence of dimethyl sulfoxide, 30 μM Compound 1 or 30 μM Compound 2. Levels of NF-κB-induced Lucia in the cell culture supernatant were assessed with luciferase detection reagent on a plate reader. *=$p<0.05$. *=$p<0.001$. (See FIG. 9**)

Example 14: Concentrations of Compound 1 in Plasma and Brain Samples

Figure 10:
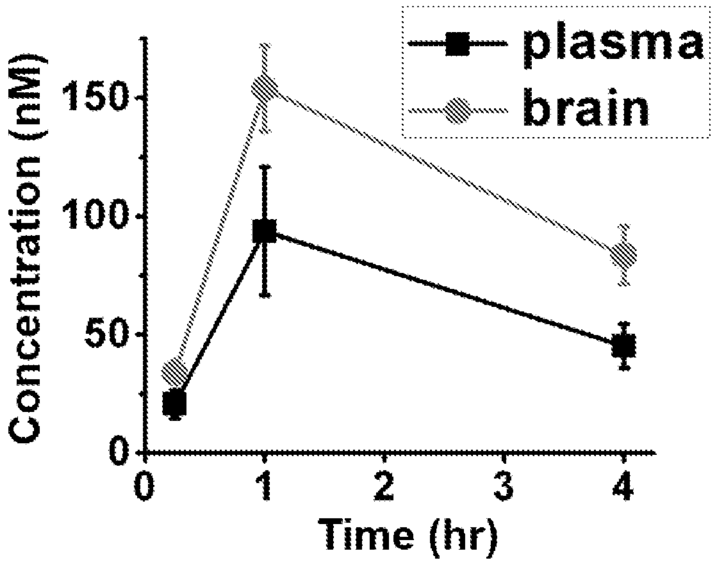
FIG. 10 depicts the concentrations of Compound 1 in mouse plasma and brain samples.

Compound 1 was administered s.c. to C57/BL6 mice and plasma and brain samples were processed and analyzed using standard bioanalytical protocols. Three mice were sacrificed at time points: 15 min, 1 hr and 4 hr. Blood was collected into lithium heparin tubes for plasma collection. Brain samples were homogenized prior to extraction using a FastPrep-24 tissue homogenizer. Plasma and brain homogenates were extracted by protein precipitation with acetonitrile containing verapamil as internal standard (IS). After vortexing for 10 min, samples were transferred to a 96 well filter plate and filtered using a centrifuge. Filtrates were analyzed by LC/MS/MS. The compounds were quantified with software using calibration curves. Compound 1 plasma (■) and brain (•) concentrations are presented. (See FIG. 10) Animal body weight and clinical observations appeared normal throughout the study.

Example 15: Experimental Autoimmune Encephalomyelitis Animal Studies

Compound 1 enhanced recovery of animals in the experimental autoimmune encephalomyelitis animal model of neuroinflammation. Experimental autoimmune encephalomyelitis is mediated by $CD4^{+}$ T cells specific for myelin-derived antigens which cause paralysis by central nervous system inflammation, demyelination of neurons, axonal damage, and neurodegeneration. C57/Bl6 mice were induced for neuroinflammation by immunization with the myelin oligodendrocyte glycoprotein $MOG_{35-55}$ in complete Freud's adjuvant followed by administration of pertussis toxin in phosphate buffered saline. 5 mg/kg Compound 1 prepared for in vivo administration by dissolving Compound 1 in 2.3046 mL of a mixture of 20 g of propylene glycol, 20 g of polyethylene glycol 400 and 1 g of Tween 80, and then 3.7854 mL of 0.9% saline while stirring.

Compound 1 was administered i.p. daily starting on day −1.

Clinical score is a representation of neuroinflammatory paralysis. 0.0=No obvious changes in motor function compared to non-immunized mice. 0.5=Tip of tail is limp. 1.0=Limp tail. 1.5=Limp tail and hind leg inhibition. 2.0=Limp tail and weakness of hind legs. 2.5=Limp tail and dragging of hind legs. 3.0=Limp tail and almost complete paralysis of hind legs. 3.5=Limp tail and complete paralysis of hind legs. In addition to: Mouse is moving around the cage, but when placed on its side, is unable to right itself. Hind legs are together on one side of body. 4.0=Limp tail, complete hind leg and partial front leg paralysis.

Figure 11:
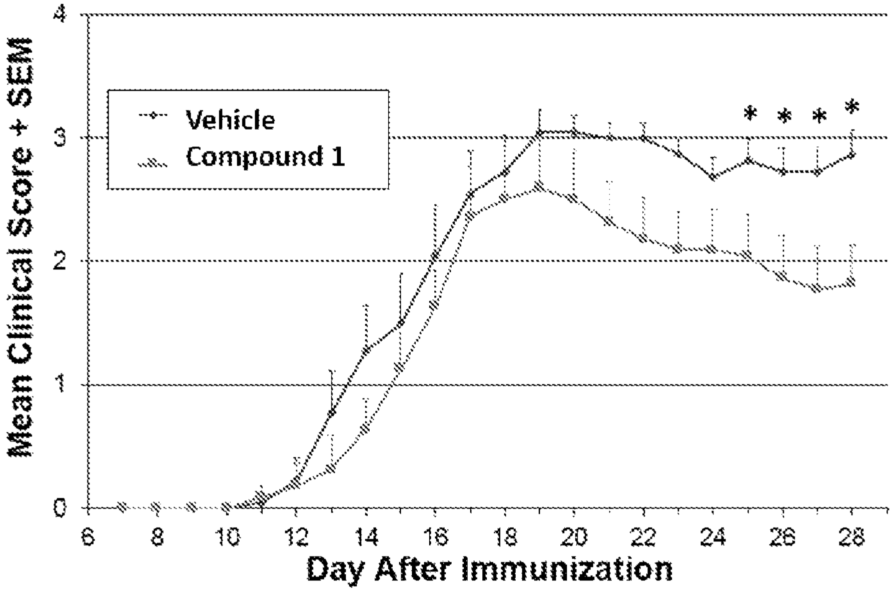
FIG. 11 depicts the neuroprotection provided by Compound 1 in an experimental autoimmune encephalomyelitis animal model of neuroinflammation.

Daily i.p. administration of Compound 1 (■) demonstrated significant neuroprotection compared to vehicle-treated (♦) mice in the experimental autoimmune encephalomyelitis animal model of neuroinflammation. (See FIG. 11) One hour after the final Compound 1 dose, LC/MS/MS bioanalysis revealed that Compound 1 levels were 38.0±4.0 nM in the brain and 23.3±3.1 nM in the plasma. *=$p<0.05$.

The examples and embodiments described herein are for illustrative purposes only and various modifications or changes suggested to persons skilled in the art are to be included within the spirit and purview of this application and scope of the appended claims.

What is claimed is:

1. A compound having the structure of Formula (I), or a pharmaceutically acceptable salt or solvate thereof:

Formula (I)

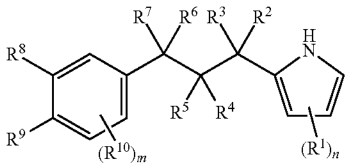

wherein, each $R^1$ is independently H, halogen, $C_1$-$C_6$alkyl, $C_1$-$C_6$fluoroalkyl, $C_1$-$C_6$deuteroalkyl, $C_3$-$C_6$cycloalkyl, $C_1$-$C_6$hydroxyalkyl, or $C_1$-$C_6$heteroalkyl;

$R^2$ is $C_1$-$C_6$alkoxy or hydroxy;

$R^3$ is $C_1$-$C_6$alkoxy or hydroxy;

or $R^2$ and $R^3$ are taken together with the carbon atom to which they are attached to form —C(=O)—, —C(=$NR^{13}$)—, —C(=N—$OR^{13}$)—, or a heterocyclic ring containing 2 O atoms;

$R^{13}$ is H or $C_1$-$C_6$alkyl;

$R^4$ is H, halogen, $C_1$-$C_6$alkyl, $C_1$-$C_6$fluoroalkyl, or $C_1$-$C_6$deuteroalkyl;

$R^5$ is H, halogen, $C_1$-$C_6$alkyl, $C_1$-$C_6$fluoroalkyl, or $C_1$-$C_6$deuteroalkyl;

or $R^4$ and $R^5$ are taken together with the carbon atom to which they are attached to form a substituted or unsubstituted $C_3$-$C_6$cycloalkyl ring, or a substituted or unsubstituted $C_3$-$C_6$heterocyclic ring containing 1 or 2 heteroatoms selected from —O—, —$NR^{12}$— and —S—;

$R^6$ is H, halogen, $C_1$-$C_6$alkyl, $C_1$-$C_6$fluoroalkyl, or $C_1$-$C_6$deuteroalkyl;

$R^7$ is H, halogen, $C_1$-$C_6$alkyl, $C_1$-$C_6$fluoroalkyl, or $C_1$-$C_6$deuteroalkyl;

or $R^6$ and $R^7$ are taken together with the carbon atom to which they are attached to form a substituted or unsubstituted $C_3$-$C_6$cycloalkyl ring, or a substituted or unsubstituted $C_3$-$C_6$heterocyclic ring containing 1 or 2 heteroatoms selected from —O—, —$NR^{12}$— and —S—;

$R^8$ is halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —CN, —$NO_2$, —OH, —$OR^{11}$, —$SR^{11}$, —S(=O)$R^{11}$, —S(=O)$_2R^{11}$, —S(=O)$_2$N($R^{12}$)$_2$, —$NR^{12}$S(=O)$_2R^{11}$, —C(=O)$R^{11}$, —OC(=O)$R^{11}$, —$CO_2R^{12}$, —$OCO_2R^{11}$, —N($R^{12}$)$_2$, —C(=O)N($R^{12}$)$_2$, —OC(=O)N($R^{12}$)$_2$, —NHC(=O)$R^{11}$, or —NHC(=O)$OR^{11}$;

$R^9$ is halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —CN, —$NO_2$, —OH, —$OR^{11}$, —$SR^{11}$, —S(=O)$R^{11}$, —S(=O)$_2R^{11}$, —S(=O)$_2$N($R^{12}$)$_2$, —$NR^{12}$S(=O)$_2R^{11}$, —C(=O)$R^{11}$, —OC(=O)$R^{11}$, —$CO_2R^{12}$, —$OCO_2R^{11}$, —N($R^{12}$)$_2$, —C(=O)N($R^{12}$)$_2$, —OC(=O)N($R^{12}$)$_2$, —NHC(=O)$R^{11}$, or —NHC(=O)$OR^{11}$;

each $R^{10}$ is independently H, halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —CN, —$NO_2$, —OH, —$OR^{11}$, —$SR^{11}$, —S(=O)$R^{11}$, —S(=O)$_2R^{11}$, —S(=O)$_2$N($R^{12}$)$_2$, —$NR^{12}$S(=O)$_2R^{11}$, —C(=O)$R^{11}$, —OC(=O)$R^{11}$, —$CO_2R^{12}$, —$OCO_2R^{11}$, —N($R^{12}$)$_2$, —C(=O)N($R^{12}$)$_2$, —OC(=O)N($R^{12}$)$_2$, —NHC(=O)$R^{11}$, or —NHC(=O)$OR^{11}$;

each $R^{H}$ is independently $C_1$-$C_6$alkyl, $C_1$-$C_6$fluoroalkyl, $C_1$-$C_6$deuteroalkyl, or $C_3$-$C_6$cycloalkyl;

each $R^{12}$ is independently H, $C_1$-$C_6$alkyl, $C_1$-$C_6$fluoroalkyl, $C_1$-$C_6$deuteroalkyl, or $C_3$-$C_6$cycloalkyl;

n is 0, 1, 2, or 3; and m is 0, 1, 2, or 3.

2. The compound of claim 1, or a pharmaceutically acceptable salt or solvate thereof, wherein:

each $R^1$ is independently H, halogen, $C_1$-$C_6$alkyl, $C_1$-$C_6$fluoroalkyl, $C_3$-$C_6$cycloalkyl;

$R^2$ and $R^3$ are taken together with the carbon atom to which they are attached to form —C(=O)—, —C(=$NR^{13}$)—, —C(=N—$OR^{13}$)—, or a heterocyclic ring containing 2 O atoms;

$R^{13}$ is H or $C_1$-$C_6$alkyl;

$R^4$ is H, halogen, $C_1$-$C_6$alkyl, $C_1$-$C_6$fluoroalkyl, or $C_1$-$C_6$deuteroalkyl;

$R^5$ is H, halogen, $C_1$-$C_6$alkyl, $C_1$-$C_6$fluoroalkyl, or $C_1$-$C_6$deuteroalkyl;

$R^6$ is H, halogen, $C_1$-$C_6$alkyl, $C_1$-$C_6$fluoroalkyl, or $C_1$-$C_6$deuteroalkyl; and $R^7$ is H, halogen, $C_1$-$C_6$alkyl, $C_1$-$C_6$fluoroalkyl, or $C_1$-$C_6$deuteroalkyl.

3. The compound of claim 1, or a pharmaceutically acceptable salt or solvate thereof, wherein:

each $R^1$ is independently H, F, Cl, Br, or $C_1$-$C_6$alkyl.

4. The compound of claim 1, or a pharmaceutically acceptable salt or solvate thereof, wherein:

$R^2$ and $R^3$ are taken together with the carbon atom to which they are attached to form —C(=O)—, —C(=NH)—, —C(=N—OH)—, or

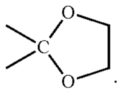

5. The compound of claim 1, or a pharmaceutically acceptable salt or solvate thereof, wherein:

$R^4$ is H or $C_1$-$C_6$alkyl;

$R^5$ is H or $C_1$-$C_6$alkyl;

$R^6$ is H or $C_1$-$C_6$alkyl; and $R^7$ is H or $C_1$-$C_6$alkyl.

6. The compound of claim 1, or a pharmaceutically acceptable salt or solvate thereof, wherein:

$R^8$ is halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —OH, —$OR^{11}$, —$SR^{11}$, —S(=O)$R^{11}$, —S(=O)$_2R^{11}$, —C(=O)$R^{11}$, —$CO_2R^{12}$, —N($R^{12}$)$_2$, or —C(=O)N($R^{12}$)$_2$.

7. The compound of claim 1, or a pharmaceutically acceptable salt or solvate thereof, wherein:

$R^9$ is halogen, $C_1$-$C_6$alkyl, $C_1$-$C_6$hydroxyalkyl, $C_1$-$C_6$heteroalkyl, —CN, —$NO_2$, —OH, —$OR^{11}$, —$SR^{11}$, —S(=O)$R^{11}$, —S(=O)$_2R^{11}$, —S(=O)$_2$N($R^{12}$)$_2$, —$NR^{12}$S(=O)$_2R^{11}$, —C(=O)$R^{11}$, —OC(=O)$R^{11}$, —$CO_2R^{12}$, —$OCO_2R^{11}$, —N($R^{12}$)$_2$, —C(═O)N($R^{12}$)$_2$, —OC(═O)N($R^{12}$)$_2$, —NHC(═O)$R^{11}$, or —NHC(═O)O$R^{11}$.

8. The compound of claim 1, or a pharmaceutically acceptable salt or solvate thereof, wherein:

each $R^{10}$ is independently H, halogen, $C_1$-$C_6$alkyl, $C_1$-$C_6$fluoroalkyl, $C_1$-$C_6$deuteroalkyl, $C_1$-$C_6$cycloalkyl, $C_1$-$C_6$hydroxyalkyl, $C_1$-$C_6$heteroalkyl, —OH, —O$R^{11}$, —S$R^{11}$, —S(═O)$R^{11}$, —S(═O)$_2R^{11}$, —C(═O)$R^{11}$, —$CO_2R^{12}$, —N($R^{12}$)$_2$, or —C(═O)N($R^{12}$)$_2$.

9. The compound of claim 1, or a pharmaceutically acceptable salt or solvate thereof, wherein:

n is 2 or 3; and m is 1.

10. The compound of claim 1, or a pharmaceutically acceptable salt or solvate thereof, wherein the compound has the following structure of Formula (II):

Formula (II)

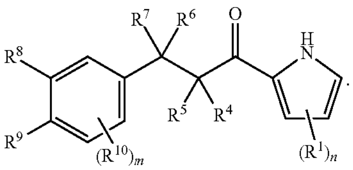

11. The compound of claim 1, or a pharmaceutically acceptable salt or solvate thereof, wherein the compound is:

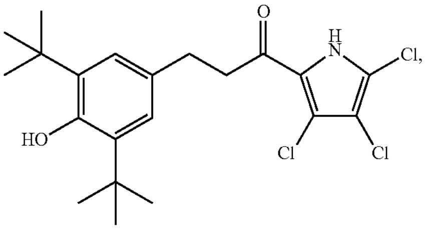

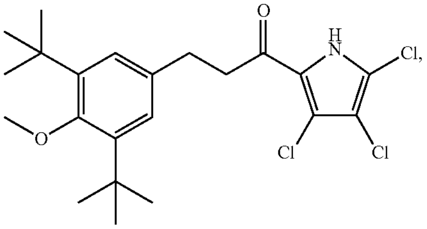

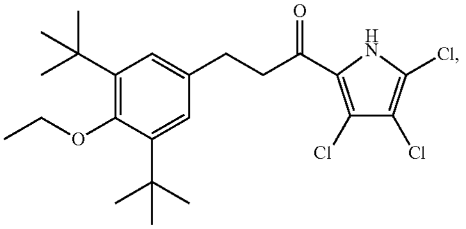

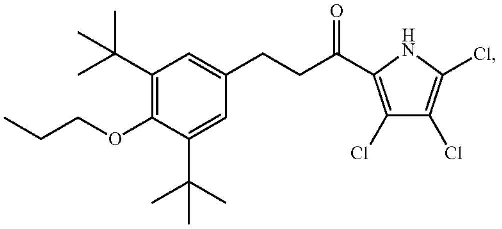

-continued

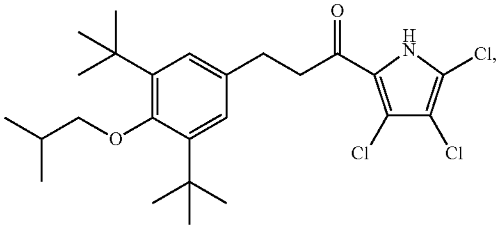

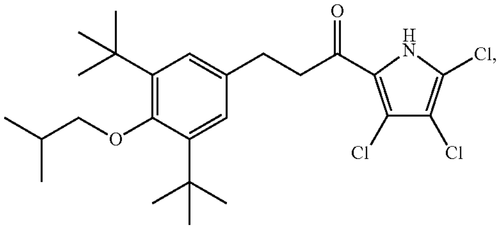

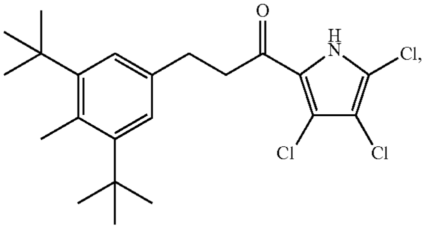

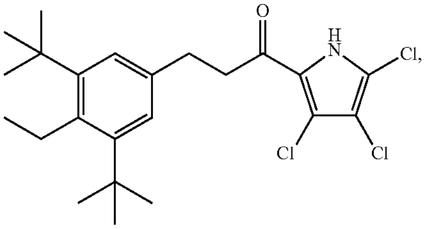

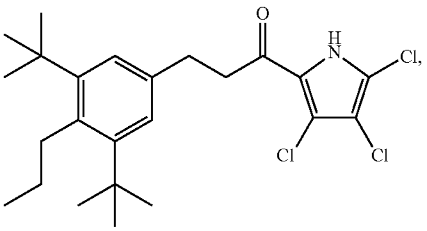

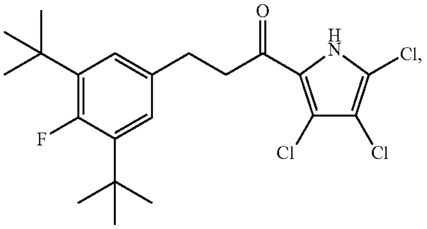

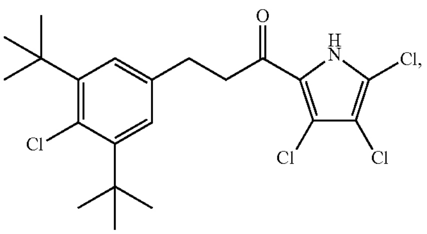

-continued
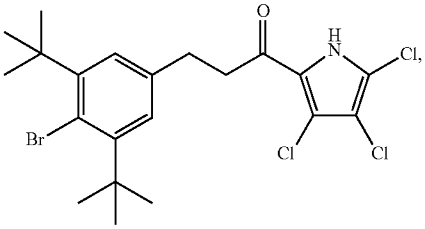
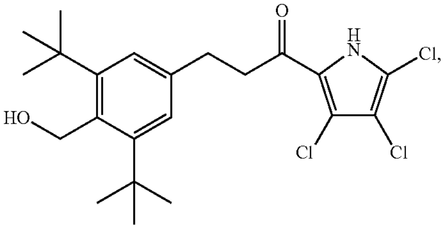
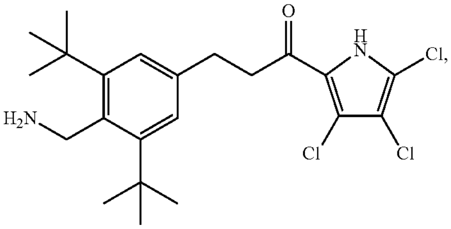
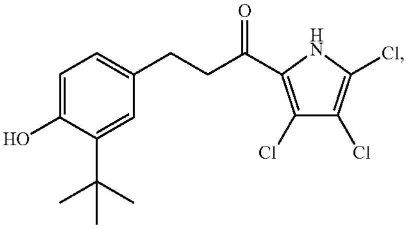
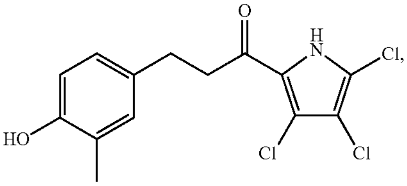
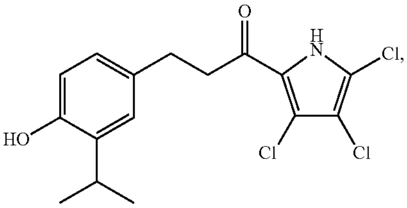
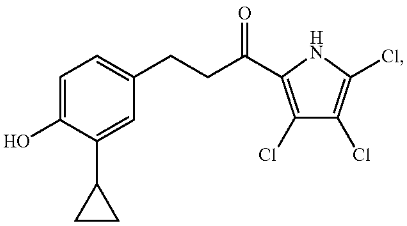
-continued
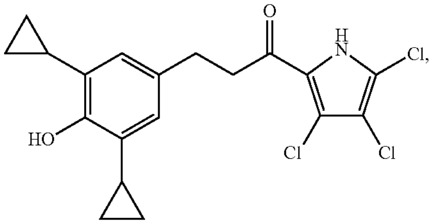
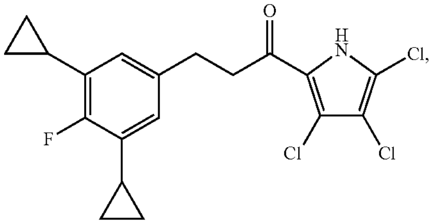
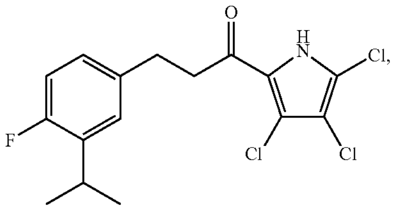
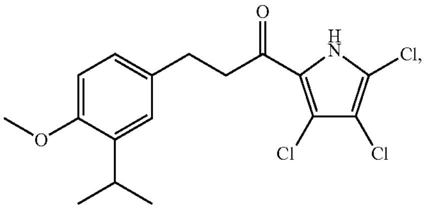
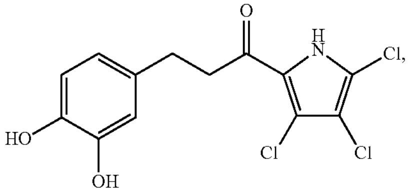
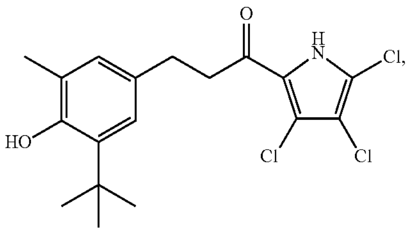
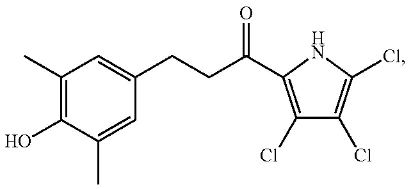
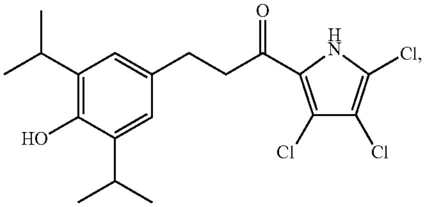

-continued
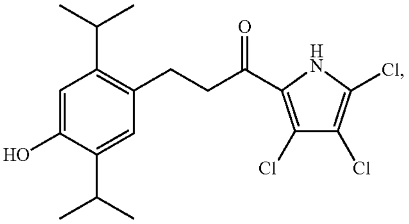
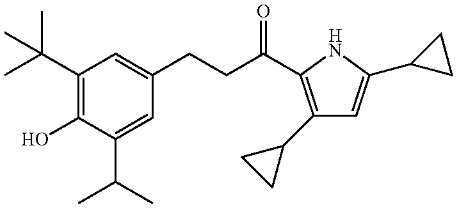
,
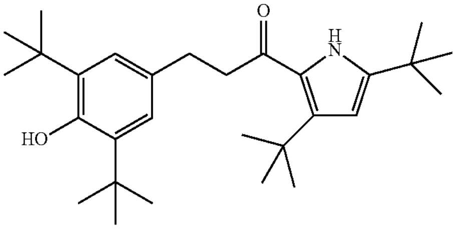
,
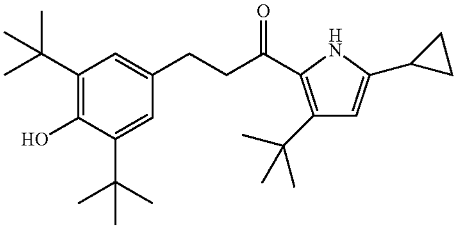
,
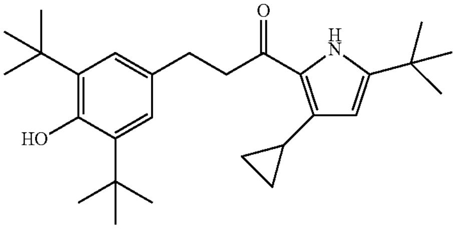
,
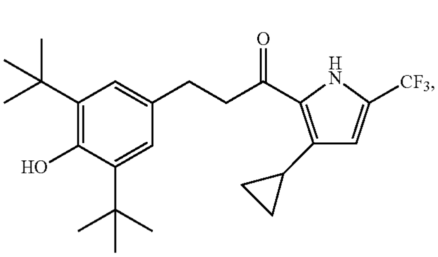
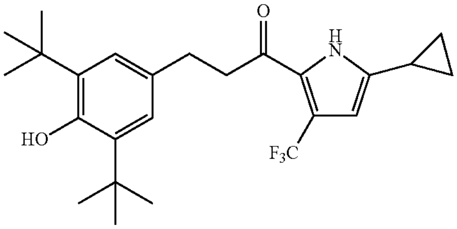
,
-continued
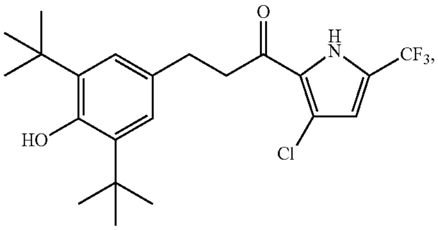
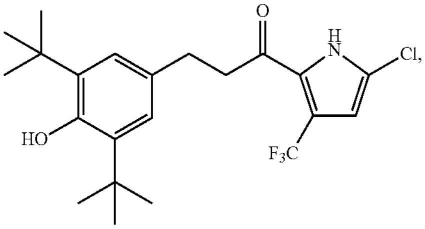
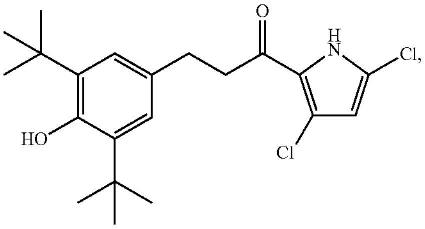
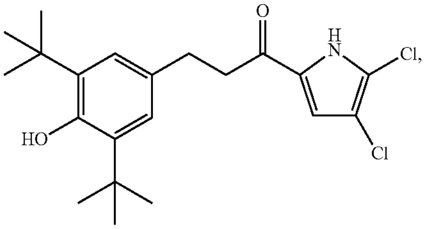
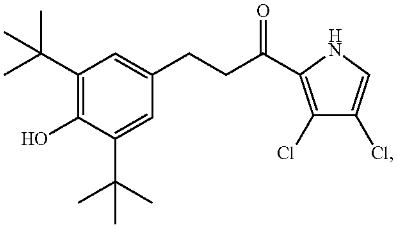
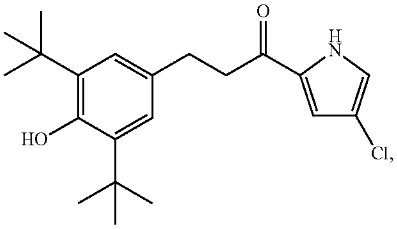
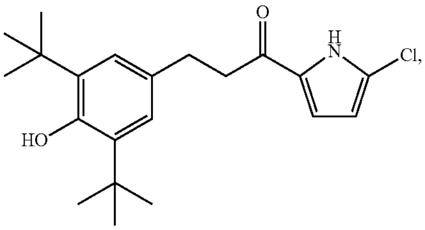

-continued
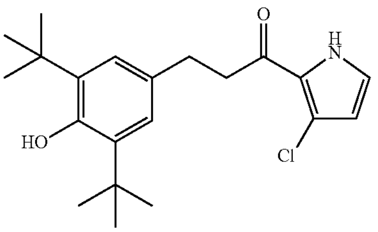
,
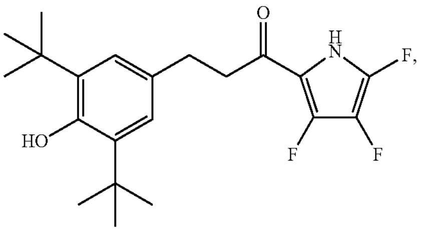
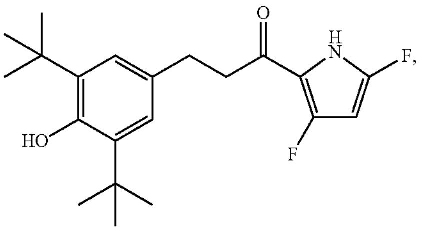
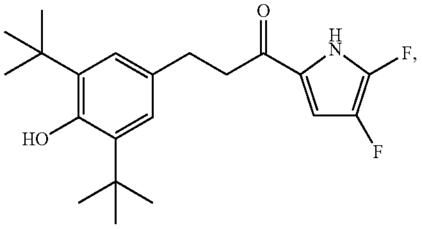
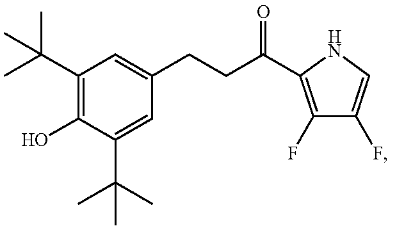
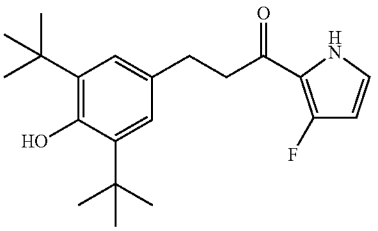
,
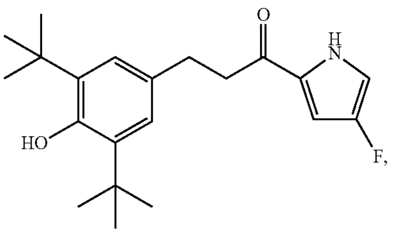
-continued
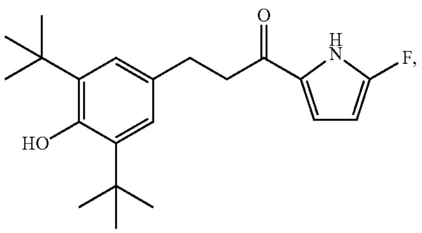
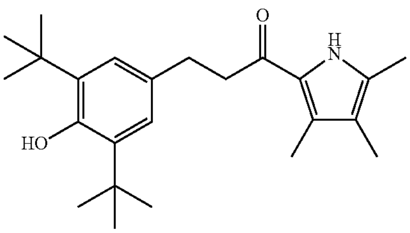
,
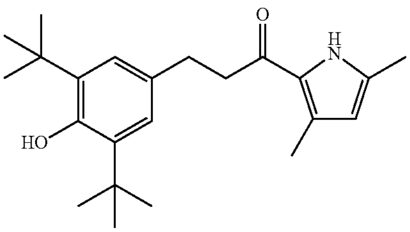
,
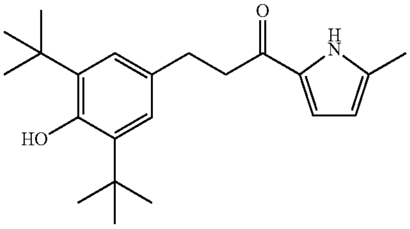
,
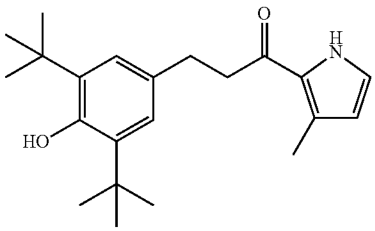
,
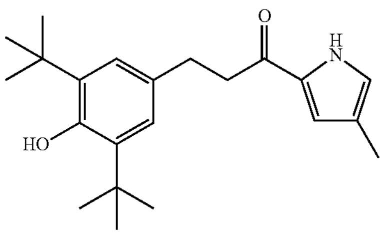
,
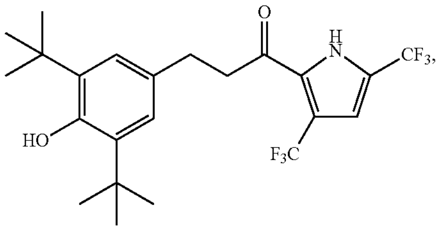

-continued
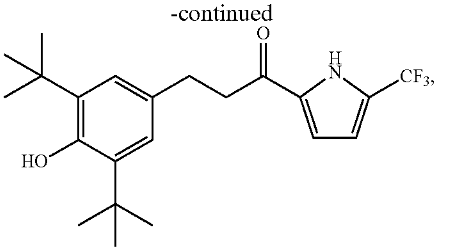
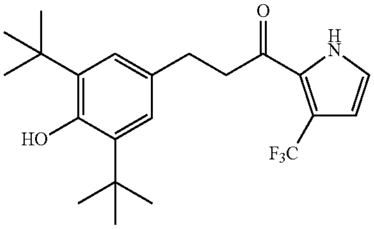
,
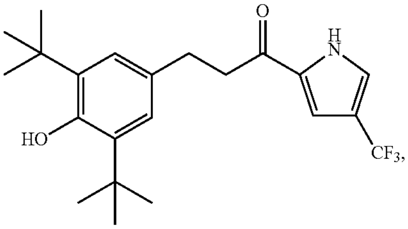
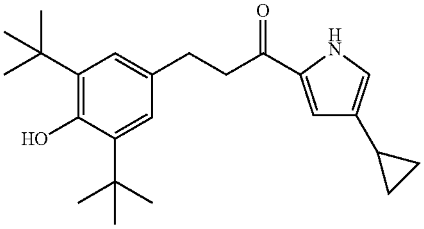
,
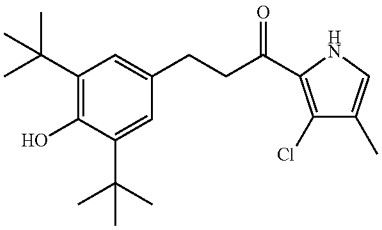
,
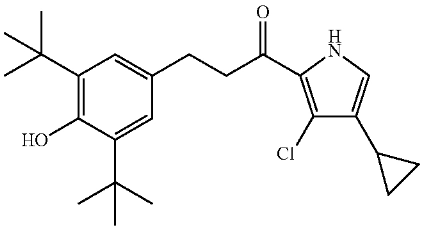
,
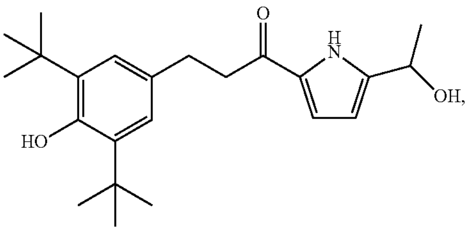
-continued
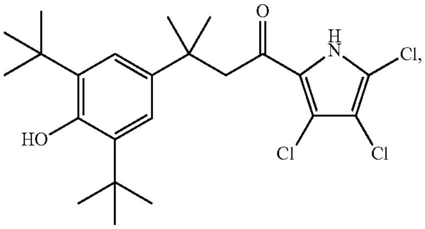
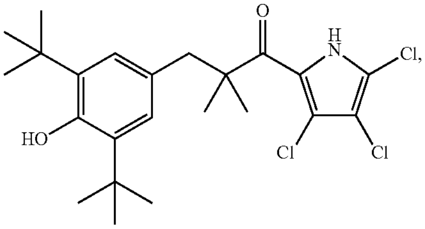
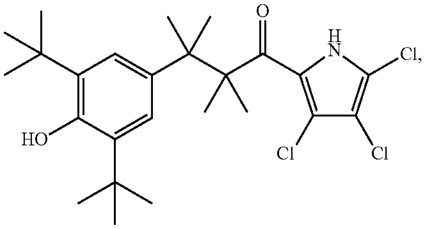
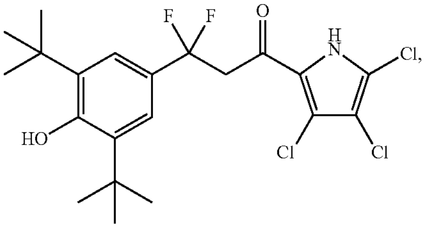
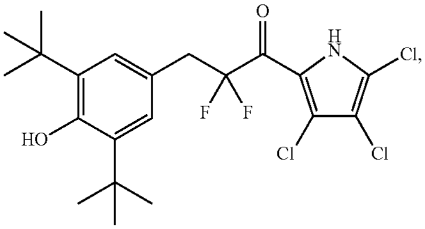
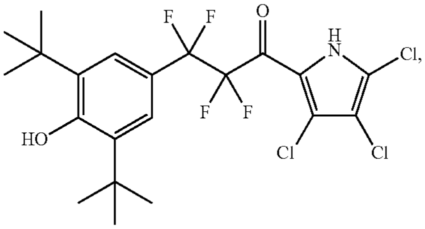
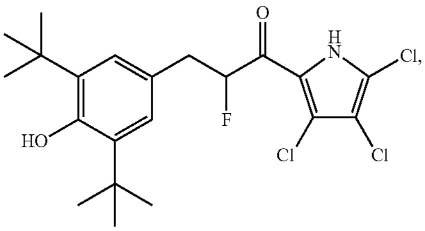

-continued

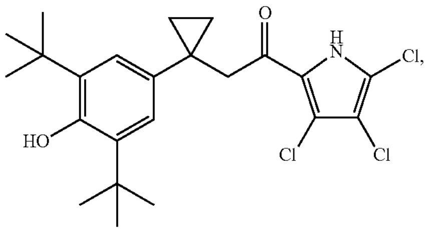

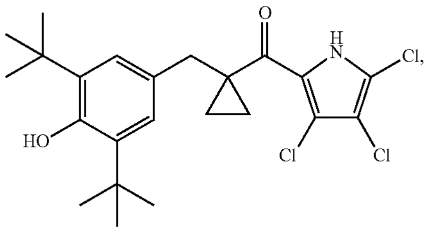

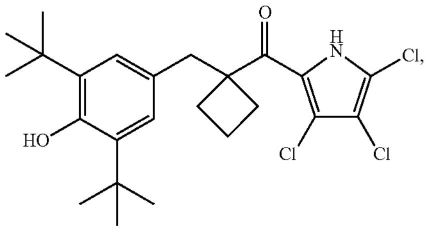

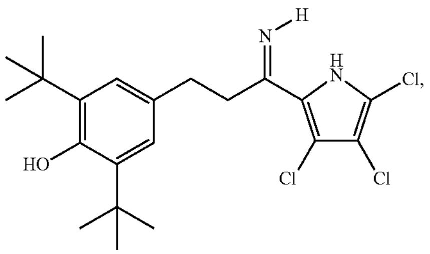

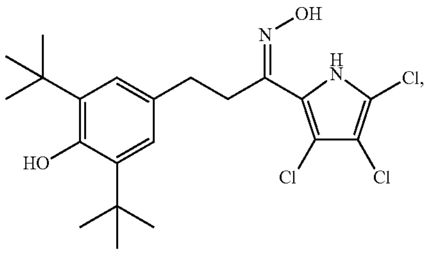

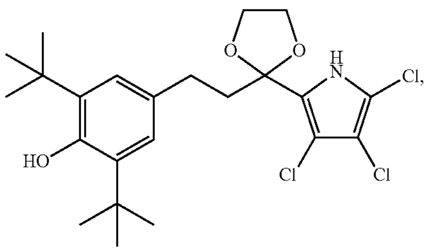

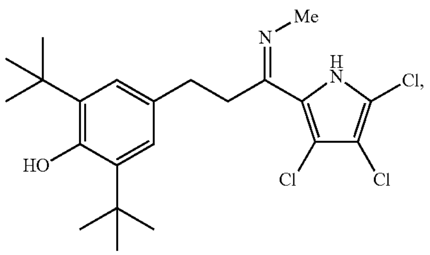

-continued

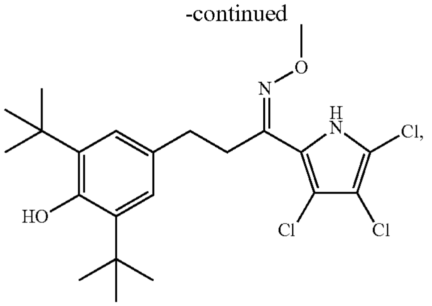

or

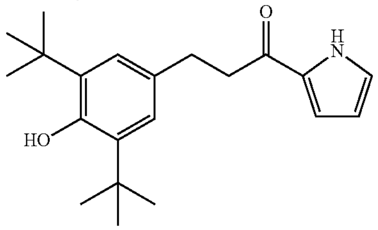

.

12. A pharmaceutical composition comprising a compound of claim 1, or a pharmaceutically acceptable salt, or solvate thereof, and at least one pharmaceutically acceptable excipient.

13. A method of treating a $Ca^{2+}$ release-activated $Ca^{2+}$ (CRAC) channel-associated disease or disorder in a subject having said disease or disorder, comprising administering a therapeutically effective amount of a compound of claim 1, or a pharmaceutically acceptable salt, or solvate thereof, to the subject.

14. The method of claim 13, wherein the $Ca^{2+}$ release activated $Ca^{2+}$ (CRAC) channel-associated disease or disorder is an immune system-related disease or disorder involving inflammation, cancer or other proliferative disease, a hepatic disease or disorder, a renal disease or disorder, or an inflammatory lung disorder.

15. The method of claim 13, wherein the $Ca^{2+}$ release activated $Ca^{2+}$ (CRAC) channel-associated disease or disorder is inflammation, glomerulonephritis, uveitis, a hepatic diseases or disorders, a renal diseases or disorders, an inflammatory lung disorder, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, allogeneic or xenogeneic transplantation, graft rejection, graft-versus-host disease, lupus pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis, atopic dermatitis, asthma, Sjogren's syndrome, organ transplant rejection, multiple sclerosis, Guillain-Barre, autoimmune uveitis, autoimmune hemolytic anemia, pernicious anemia, autoimmune thrombocytopenia, temporal arteritis, anti-phospholipid syndrome, vasculitides such as Wegener's granulomatosis, Behcet's disease, psoriasis, dermatitis herpetiformis, pemphigus vulgaris, vitiligo, Crohn's disease, colitis, ulcerative colitis, primary biliary cirrhosis, autoimmune hepatitis, Type 1 or immune-mediated diabetes mellitus, Grave's disease, Hashimoto's thyroiditis, autoimmune oophoritis and orchitis, autoimmune disorder of the adrenal gland, systemic lupus erythematosus, polymyositis, dermatomyositis, ankylosing spondylitis, transplant rejection, skin graft rejection, arthritis, bone diseases associated with increased bone resorption, ileitis, Barrett's syndrome, adult respiratory distress syndrome, chronic obstructive airway disease; corneal dystrophy, trachoma, onchocerciasis, sympathetic ophthalmitis, endophthalmitis; gingivitis, periodontitis; tuberculosis; leprosy; uremic complications, nephrosis; sclerodermatitis, psoriasis, chronic demyelinating diseases of the nervous system, AIDS-related neurodegeneration, Alzheimer's disease, infectious meningitis, encephalomyelitis, Parkinson's disease, Huntington's disease, amyotrophic lateral sclerosis viral or autoimmune encephalitis; autoimmune disorders, immunecomplex vasculitis, systemic lupus and erythematodes; systemic lupus erythematosus (SLE); cardiomyopathy, ischemic heart disease hypercholesterolemia, atherosclerosis, preeclampsia; chronic liver failure, brain and spinal cord trauma, or cancer, wherein the cancer is a hematopoietic tumor of lymphoid lineage, leukemia, acute lymphocytic leukemia, acute lymphoblastic leukemia, B cell lymphoma, T-cell lymphoma, Hodgkin's lymphoma, non-Hodgkin's lymphoma, hairy cell lymphoma and Burkett's lymphoma; hematopoietic tumors of myeloid lineage, acute myelogenous leukemias, chronic myelogenous leukemias, myelodysplastic syndrome, promyelocytic leukemia; carcinoma of the bladder, carcinoma of the breast, carcinoma of the colon, carcinoma of the kidney, carcinoma of the liver, carcinoma of the lung, small cell lung cancer, esophageal cancer, gall bladder cancer, ovarian cancer, pancreatic cancer, stomach cancer, cervical cancer, thyroid cancer, prostate cancer, skin cancer, squamous cell carcinoma; tumors of mesenchymal origin, fibrosarcoma, rhabdomyosarcoma; tumors of the central and peripheral nervous system, astrocytoma, neuroblastoma, schwannoma, melanoma, seminoma, teratocarcinoma, osteosarcoma, xenoderoma pigmentosum, keratoctanthoma, thyroid follicular cancer, or Kaposi's sarcoma.

16. The method of claim 13, further comprising administering one or more additional therapeutic agents to the subject.

17. A method of reducing neuroinflammation in a subject in need thereof, comprising administering a therapeutically effective amount of a compound of claim 1, or a pharmaceutically acceptable salt, or solvate thereof, to the subject.

18. The method of claim 17, wherein the subject has a neurological disease or disorder.

19. The method of claim 17, wherein the subject has Alzheimer's disease, progressive multiple sclerosis, Huntington's disease, amyotrophic lateral sclerosis, or Parkinson's disease.

20. The method of claim 17, wherein inflammation of microglia is reduced.

* * * * *